United States Patent [19]
Formoso et al.

[11] Patent Number: 5,260,189
[45] Date of Patent: Nov. 9, 1993

[54] SYNTHETIC HIV-LIKE PEPTIDES THEIR COMPOSITIONS AND USES

[75] Inventors: Carl Formoso, Anhui, China; Duane A. Olsen, Tacoma; Thomas M. Buchanan, Seattle, both of Wash.

[73] Assignee: Immunodiagnostics, Inc., Seattle, Wash.

[21] Appl. No.: 962,612

[22] Filed: Oct. 15, 1992

Related U.S. Application Data

[63] Continuation of Ser. No. 840,641, Feb. 24, 1992, abandoned, which is a continuation of Ser. No. 287,412, Dec. 20, 1988, abandoned.

[51] Int. Cl.$^5$ .......................................... G01N 33/537
[52] U.S. Cl. .......................................... 435/5; 435/7.9; 435/7.92; 435/7.93; 435/7.94; 435/974; 435/975; 530/326; 930/221
[58] Field of Search .................... 435/5, 7.9–7.94, 435/974, 975; 530/324–330; 930/221

[56] References Cited

U.S. PATENT DOCUMENTS

| | | | |
|---|---|---|---|
| 4,679,783 | 12/1986 | Cosand | 530/324 |
| 4,735,896 | 4/1988 | Wang et al. | 435/5 |
| 4,753,873 | 6/1988 | Beltz et al. | 435/5 |
| 4,812,556 | 3/1989 | Vahlne et al. | 530/324 |

FOREIGN PATENT DOCUMENTS

| | | |
|---|---|---|
| 0278148 | 8/1988 | European Pat. Off. |
| WO87/06005 | 8/1987 | PCT Int'l Appl. |
| WO88/05440 | 7/1988 | PCT Int'l Appl. |

OTHER PUBLICATIONS

R. S. Smith, et al., "Antibody to a Synthetic Oligopeptide in Sub Human Immunodeficiency Virus Infection," *J Clin Microbiol* 25:1498–1504, 1987.

J. W. Gnann, Jr., et al., "Diagnosis of AIDS by Using a 12-Amino Acid Peptide Representing an Immunodominant Epitope of the Human Immunodeficiency Virus," *J Infect Dis* 156:261–267, 1987.

J. W. Gnann, Jr., et al., "Synthetic Peptide Immunoassay Distinguishes HIV Type 1 and HIV Type 2 Infections," *Science* 237:1346–1349, 1987.

M. Zweig, et al., "Comparative Analysis of gp41 Antigens by Enzyme-Linked Immunosorbent Assays for Detecting Antibodies to Human Immunodeficiency Virus Type 1," *AIDS Research and Human Retroviruses* 4:(6), 487–492, 1988.

*Human Retroviruses and AIDS 1989*, G. Myers et al. eds., Theoretical Biology and Biophysics, Los Alamos, N.M., publishers, p. II-50 and p. II-56.

L. Ratner et al., "Complete nucleotide sequence of the AIDS virus, HTLV-III," *Nature* 313:277–284, 1985.

S. Wain-Hobson et al., "Nucleotide Sequence of the AIDS Virus, LAV," *Cell* 40:9–17, 1985.

R. Sanchez-Pescador et al., "Nucleotide Sequence and Expression of an AIDS-Associated Retrovirus (ARV-2)," *Science* 227:484–492, 1985.

M. Guyader et al., "Genome organization and transactivation of the human immunodeficiency virus type 2," *Nature* 326:662–669, 1987.

Primary Examiner—Christine M. Nucker
Assistant Examiner—Jeffrey Stucker
Attorney, Agent, or Firm—Christensen, O'Connor, Johnson & Kindness

[57] ABSTRACT

Highly immunoreactive regions of gp41 of HIV-1, gp32 of HIV-2 and p24 of HIV-1 were identified using synthetic peptides. Superior immunoassay performance is obtained with these peptides linked to carrier proteins as compared to use of the free peptides. Additional natural and unnatural variants of these reactive regions to define a set of peptides that, as cysteine-linked peptide-protein conjugates, provide optimal immunoassay performance including high immunoreactivity with HIV antibody positive samples, low reactivity with negative samples, high discrimination between positives and negatives, and high specificity. These peptide conjugates further permit simultaneous detection of HIV-1 and HIV-2 antibodies, and make possible rapid and simple test formats that require no instrumentation for detection of these antibodies.

9 Claims, 20 Drawing Sheets

| Peptide # | Sequence | Natural (N) or Unnatural (U) | % Inhibition wt of free peptide 10 μg | 1 μg |
|---|---|---|---|---|
| 2S09 | I W G C S G K L I C T T A V P G C | N | 100 | 100 |
| 4S35 | L W G C S G K L I C T T A V P G C | U | 100 | 82 |
| 4S36 | Y W G C S G K L I C T T A V P G C | U | 100 | 94 |
| 4S37 | I Y G C S G K L I C T T A V P G C | U | 93 | 70 |
| 4S38 | I E G C S G K L I C T T A V P G C | U | 98 | 82 |
| 4S40 | I W A C S G K L I C T T A V P G C | U | 94 | 64 |
| 4S41 | I W G S S G K L I C T T A V P G C | U | 78 | 17 |
| 4S42 | I W G K S G K L I C T T A V P G C | U | 63 | 10 |
| 4S43 | I W G C T G K L I C T T A V P G C | U | 100 | 90 |
| 4S44 | I W G C S A K L I C T T A V P G C | U | 91 | 57 |
| 4S45 | I W G C S G E L I C T T A V P G C | U | 90 | 89 |
| 4S46 | I W G C S G K L I C T T A V P G C | U | 93 | 89 |
| 4S47 | I W G C S G K Y I C T T A V P G C | U | 81 | 40 |
| 4S48 | I W G C S G K L L C T T A V P G C | U | 100 | 75 |
| 4S49 | I W G C S G K L V C T T A V P G C | U | 96 | 85 |
| 4S50 | I W G C S G K L I S T T A V P G C | U | 45 | 13 |
| 4S51 | I W G C S G K L I K T T A V P G C | U | 32 | 0 |
| 4S52 | I W G C S G K L I C S T A V P G C | U | 93 | 72 |
| 4S53 | I W G C S G K L I C T S A V P G C | U | 93 | 75 |
| 4S54 | I W G C S G K L I C T T G V P G C | U | 98 | 85 |
| 4S55 | I W G C S G K L I C T T A L P G C | U | 87 | 87 |
| 4S56 | I W G C S G K L I C T T A L P G C | U | 96 | 87 |

| Peptide # | Sequence | Avg A492 HIV+/HIV- |
|---|---|---|
| KLH-MBS Peptide Conjugates | | |
| 2S04 | K D Q Q L L G I W G C S G K L G C | 1.15/0.13 |
| 2S06 | L L G I W G C S G K L I C T T G L | 1.09/0.09 |
| 2S07 | L G I W G C S G K L I C T T A G C | 1.13/0.13 |
| 2S09 | I W G C S G K L I C T T A V P G C | 1.53/0.13 |
| 2S10 | W G C S G K L I C T T A V P W G C | 1.37/0.10 |
| BSA-SMCC Peptide Conjugates | | |
| 4S24 | I K Q L Q A R I L A V E R Y L K D Q Q G C | 0.46/0.15 |
| 2S01 | A V E R Y L K D Q Q L L G C | 0.70/0.19 |
| 2S02 | E R Y L K D Q Q L L G I W G C | 0.40/0.15 |
| 2S03 | Y L K D Q Q L L G I W G C S G C | 0.51/0.15 |
| 2S04 | K D Q Q L L G I W G C S G K L G C | 1.74/0.14 |
| 4S25 | R I L A V E R Y L K D Q Q L L G I W G C S G K L I C G C | 1.64/0.15 |
| 3S36 | Q Q L L G I W G C S G K L I C G C | 1.75/0.13 |
| 2S06 | L L G I W G C S G K L I C T T G C | 1.66/0.14 |
| 2S07 | L G I W G C S G K L I C T T A G C | 1.66/0.13 |
| 2S09 | I W G C S G K L I C T T A V P G C | 1.93/0.12 |
| 2S11 | W G C S G K L I C T T A V P W N G C | 1.79/0.15 |
| 3S51 | G C S G K L I C T T A V P W N A G C | 1.82/0.12 |
| 2S13 | C S G K L I C T T A V P W N A S G C | 1.78/0.13 |
| 3S55 | S G K L I C T T A V P W N A S W G C | 1.76/0.14 |
| 2S15 | G K L I C T T A V P W N A S W S G C | 1.76/0.14 |

| Peptide # | Sequence | Natural (N) or Unnatural (U) | % Inhibition wt of free peptide 10 μg | % Inhibition wt of free peptide 1 μg |
|---|---|---|---|---|
| 2S09 | L W G C S G K L I – C T T A V P G C | N | 100 | 100 |
| 4S35 | L W G C S G K L L – C T T A V P G C | U | 100 | 82 |
| 4S36 | V W G C S G K L L – C T T A V P G C | U | 100 | 94 |
| 4S37 | – Y G C S G K L L – C T T A V P G C | U | 93 | 70 |
| 4S38 | – E G A S G K L L – C T T A V P G C | U | 98 | 82 |
| 4S40 | – W A C S G K L L – C T T A V P G C | U | 94 | 64 |
| 4S41 | – W G C S G K L L L C T T A V P G C | U | 78 | 17 |
| 4S42 | – W G S S G K L V – C T T A V P G C | U | 63 | 10 |
| 4S43 | – W G M T G K L L – C T T A V P G C | U | 100 | 90 |
| 4S44 | – W G C S A K L L – C T T A V P G C | U | 91 | 57 |
| 4S45 | – W G C S G R L L – C T T A V P G C | U | 90 | 89 |
| 4S46 | – W G C S G K L L V C T T A V P G C | U | 93 | 89 |
| 4S47 | – W G C S G K L L – C T T A V P G C | U | 81 | 40 |
| 4S48 | – W G C S G K L L – C S T A V P G C | U | 100 | 75 |
| 4S49 | – W G C S G K L L – C M T A V P G C | U | 96 | 85 |
| 4S50 | – W G C S G K L L – S S T A V P G C | U | 45 | 13 |
| 4S51 | – W G C S G K L L – C T S A V P G C | U | 32 | 0 |
| 4S52 | – W G C S G K L L – C T T G A V P G C | U | 93 | 72 |
| 4S53 | – W G C S G K L L – C T T A V P G C | U | 93 | 75 |
| 4S54 | – W G C S G K L L – C T T A G V P G C | U | 98 | 85 |
| 4S55 | – W G C S G K L L – C T T A V L P G C | U | 87 | 87 |
| 4S56 | – W G C S G K L L – C T T A V L P G C | U | 96 | 87 |

*Fig. 3.*

| Peptide # | Sequence | | | | | | | | | | | | Natural (N) or Unnatural (U) | % Inhibition | | | |
|---|---|---|---|---|---|---|---|---|---|---|---|---|---|---|---|---|---|
| | | | | | | | | | | | | | | L Var (2S09) | | H Var (5S67) | |
| | | | | | | | | | | | | | | 10μg | 0.5μg | 10μg | 0.5μg |
| 2S09 (L Var) | L | W | G | C | S | G | K | L | I | C | T | T | A | V | P | G | C | N | 99 | 93 | 99 | 91 |
| 5S51 | E | W | G | C | S | G | K | L | I | C | T | I | V | P | G | C | | N | 97 | 86 | 93 | 85 |
| 5S52 | I | W | G | C | S | G | K | L | I | C | T | I | A | V | P | G | C | N | 100 | 90 | 95 | 94 |
| 5S53 | E | W | G | C | S | G | K | L | I | C | T | A | V | P | G | C | | N | 97 | 95 | 94 | 82 |
| 5S54 | I | W | G | C | S | G | K | H | I | C | T | T | V | P | G | C | | U | 59 | 11 | 98 | 88 |
| 5S56 | I | W | G | C | S | G | K | E | I | C | T | T | V | P | G | C | | U | 73 | 34 | 84 | 90 |
| 5S57 | I | W | G | C | S | G | K | K | I | C | T | T | E | V | P | G | C | U | 16 | 1 | 97 | 81 |
| 5S58 | I | W | G | C | S | G | K | R | I | C | T | T | V | P | G | C | | U | 57 | 0 | 94 | 78 |
| 5S59 | M | W | G | C | S | G | K | M | I | C | T | A | V | P | G | C | | U | 48 | 10 | 90 | 74 |
| 5S61 | I | W | G | C | S | G | K | Y | I | C | T | T | V | P | G | C | | N | 51 | 5 | 99 | 89 |
| 5S62 | I | W | G | C | S | G | K | P | I | C | T | A | V | P | G | C | | U | 62 | 0 | 64 | 36 |
| 5S63 | I | W | G | C | S | G | K | L | I | C | T | M | V | P | G | C | | U | 61 | 17 | 88 | 60 |
| 5S65 | I | W | G | C | S | G | K | L | I | C | T | A | V | P | G | C | | N | 97 | 70 | 96 | 82 |
| 5S66 | I | W | G | C | S | G | K | W | I | C | T | A | V | P | G | C | | U | 53 | 1 | 87 | 73 |
| 5S67 (H Var) | L | W | G | C | S | G | K | H | I | C | T | I | V | P | G | C | | N | 58 | 9 | 98 | 93 |
| 5S69 | I | W | G | C | S | G | K | N | I | C | T | A | V | P | G | C | | U | 27 | 1 | 98 | 86 |
| 5S70 | I | W | G | C | S | G | K | Q | I | C | T | A | V | P | G | C | | U | 84 | 39 | 97 | 90 |
| 5S71 | M | W | G | C | S | G | K | Y | I | C | T | I | V | P | G | C | | U | 65 | 23 | 74 | 62 |
| 5S73 | I | W | G | C | S | G | K | E | I | C | T | A | V | P | G | C | | U | 31 | 17 | 100 | 76 |
| 5S74 | I | W | G | C | S | G | K | D | I | C | T | A | V | P | G | C | | U | 10 | 0 | 88 | 60 |
| 5S75 | I | W | G | C | S | G | K | I | I | C | T | A | V | P | G | C | | U | 46 | 33 | 99 | 86 |
| 5S76 | I | W | G | C | S | G | K | M | I | C | T | A | V | P | G | C | | U | 88 | 56 | 88 | 91 |
| 5S78 | I | W | G | C | S | G | E | K | L | I | C | T | A | V | P | G | C | U | 52 | 2 | 42 | 17 |
| 5S79 | I | W | G | C | S | G | K | Q | L | I | C | T | A | V | P | G | C | U | 7 | 0 | 50 | 11 |
| 5S80 | I | W | G | C | S | G | E | H | L | I | C | T | A | V | P | G | C | U | 21 | 1 | 70 | 24 |
| 5S81 | I | W | G | C | S | G | H | R | K | L | I | C | T | A | V | P | G | C | U | 88 | 55 | 80 | 53 |
| 5S82 | I | W | G | C | S | G | H | L | I | C | T | A | V | P | G | C | | U | 74 | 6 | 42 | 6 |
| 5S83 | I | W | G | C | S | G | Q | Q | L | I | C | T | A | V | P | G | C | U | 32 | 1 | 42 | 4 |

| Peptide # | Sequence | Natural (N) or Unnatural (U) | A492 HIV+/HIV- |
|---|---|---|---|
| 2S09 (L Var) | I W G C S G K L I C T T A V P G C | N | 1.89/.14 |
| 4S35 | L W G C S G K L I C T T A V P G C | U | 1.80/.16 |
| 4S36 | V W G C S G K L I C T T A V P G C | U | 1.82/.14 |
| 4S37 | I Y G C S G K L I C T T A V P G C | U | 1.71/.15 |
| 4S38 | I F G C S G K L I C T T A V P G C | U | 1.73/.15 |
| 4S43 | I W G C T G K L I C T T A V P G C | U | 1.82/.15 |
| 4S45 | I W G C S G R L I C T T A V P G C | U | 1.74/.15 |
| 4S46 | I W G C S G K I I C T T A V P G C | U | 1.80/.14 |
| 4S48 | I W G C S G K L L C T T A V P G C | U | 1.71/.14 |
| 4S49 | I W G C S G K L V C T T A V P G C | U | 1.83/.15 |
| 4S52 | I W G C S G K L I C S T A V P G C | U | 1.77/.14 |
| 4S53 | I W G C S G K L I C T S A V P G C | U | 1.83/.15 |
| 4S54 | I W G C S G K L I C T T G V P G C | U | 1.73/.14 |
| 4S55 | I W G C S G K L I C T T A L P G C | U | 1.65/.15 |
| 4S56 | I W G C S G K L I C T T A I P G C | U | 1.56/.13 |
| 5S51 | F W G C S G K L I C T T T V P G C | N | 1.75/.15 |
| 5S52 | I W G C S G K L I C T T T V P G C | N | 1.77/.12 |
| 5S53 | F W G C S G K L I C T T A V P G C | N | 1.75/.12 |
| 5S55 | I W G C S G H L I C T T N V P G C | N | 1.52/.13 |
| 5S56 | I W G C S G K F I C T T T V P G C | U | 1.71/.14 |
| 5S60 | M W G C S G K H I C T T F V P G C | N | 1.52/.16 |
| 5S61 | I W G C S G K V I C T T A V P G C | U | 1.52/.19 |
| 5S64 | I W G C S G K I I C P T N V P G C | N | 1.69/.15 |
| 5S65 | I W G C S G K I I C T T A V P G C | U | 1.70/.13 |
| 5S67 (H Var) | I W G C S G K H I C T T T V P G C | N | 1.82/.13 |
| 5S70 | I W G C S G K Q I C T T A V P G C | U | 1.79/.13 |
| 5S75 | I W G C S G K T I C T T A V P G C | U | 1.73/.14 |
| 5S76 | I W G C S G K M I C T T A V P G C | U | 1.81/.12 |
| 5S81 | I W G C S H K L I C T T A V P G C | U | 1.75/.13 |
| ABI5 | V W G C S G K M I C T T A V P G C | U | |
| ABI4 | K D Q Q L L G V W G C S G K L G C | U | |

Fig. 4.

| Peptide # | Sequence | Avg A492 SIV+/SIV- |
|---|---|---|
| KLH-MBS Peptide Conjugates | | |
| 2S25 | A R L N S W G C A F R Q V C H G C | 1.30/0.17 |
| 2S30 | A F R Q V C H T T V P W V N D G C | 0.08/0.12 |
| BSA-SMCC Peptide Conjugates | | |
| AB18 | L Q D Q A R L N S W G C A F R G C | 1.41/0.13 |
| 2S23 | Y L D Q A R L N S W G C A F R G C | 1.42/0.13 |
| 2S24 | D Q A R L N S W G C A F R Q V C | 1.95/0.13 |
| 2S25 | A R L N S W G C A F R Q V C H G C | 1.90/0.12 |
| 2S27 | S W G C A F R Q V C H T T V P G C | 1.85/0.12 |
| 2S28 | G C A F R Q V C H T T V P W V G C | 0.92/0.13 |
| 2S30 | A F R Q V C H T T V P W V N D G C | 0.51/0.13 |
| 2S32 | R Q V C H T T V P W V N D S G C | 0.33/0.14 |
| 2S34 | V C H T T V P W V N D S L A G C | 0.40/0.14 |

Fig. 5.

| Peptide # | Sequence | Natural (N) Unnatural (U) | % Inhibition wt. of free peptide 10μg | 1μg |
|---|---|---|---|---|
| 2S27 | S W G C A F R Q V C H T T V P G C | N | 99 | 100 |
| 5S85 | A W G C A F R Q V C H T T V P G C | N | 97 | 99 |
| 5S86 | S W G C A F R Q V C H T S V P G C | N | 99 | 98 |
| 5S87 | S W G C A W R Q V C H T T V P G C | U | 83 | 38 |
| 5S88 | S W G C A Y R Q V C H T T V P G C | U | 88 | 58 |
| 5S89 | S W G C A H R Q V C H T T V P G C | U | 61 | 17 |
| 5S90 | S W G C A F H Q V C H T T V P G C | U | 92 | 71 |
| 5S91 | S W G C A F K Q V C H T T V P G C | U | 95 | 58 |
| 5S92 | S W G C A F R N V C H T T V P G C | U | 98 | 86 |

Fig. 9.

| Peptide # | Sequence | Natural (N) or Unnatural (U) | Avg A492 SIV+/SIV- |
|---|---|---|---|
| AB18 | L Q D Q A R L N S W G C A F R G C | N | 0.80/.12 |
| 2S23 | Y L D Q A R L N S W G C A F R G C | U | 0.77/.12 |
| 2S24 | D Q A R L N S W G C A F R Q V C | N | 1.38/.13 |
| 2S25 | A R L N S W G C A F R Q V C H G C | N | 1.36/.12 |
| 2S27 | S W G C A F R Q V C H T T V P G C | N | 1.28/.12 |
| 5S84 | S W G C A F R Q V C H T T V P G C | N | 1.26/.12 |
| 5S85 | A W G C A F R Q V C H T T V P G C | N | 1.30/.12 |
| 5S86 | S W G C A F R Q V C H T S V P G C | N | 1.44/.12 |
| 5S88 | S W G C A Y R Q V C H T T V P G C | U | 1.20/.12 |
| 5S90 | S W G C A F H Q V C H T T V P G C | U | 1.25/.12 |
| 5S91 | S W G C A F K Q V C H T T V P G C | U | 1.18/.12 |
| 5S92 | S W G C A F R N V C H T T V P G C | U | 1.34/.12 |
| AB17 | S W G C A F R Q V C T T T V P G C | U | 1.08/.12 |
| 2S30 | A F R Q V C H T T V P W V N D G C | N | 0.32/.13 |

Fig. 7.

| Peptide # | Avg A492 HIV+/HIV- Pool* | Sequences | Avg A492 HIV+/HIV- Individual |
|---|---|---|---|
| 6S68 | Pool | E P F R D Y V D R F Y K T L R G C | |
| 6S69 | | Y V D R F Y K T L R A E Q A S G C | |
| 6S70 | | Y K T L R A E Q A S Q E V K N G C | |
| 6S71 | .34/.21 | A E Q A S Q E V K N W M T E T G C | |
| 1S50 | Pool | T E T L L V Q N A N P D C K T G C | |
| 4S32 | | A N P D C K T I L K A L G P A G C | |
| 4S33 | .45/.20 | K T I L K A L G P A A T L E E G C | |
| 5S93 | Pool | I L K A L G P A A T L E E M M G C | .25/.16 |
| 5S94 | | A L G P A A T L E E M M T A C G C | 1.58/.14 |
| 5S95 | | P A A T L E E M M T A C Q G V G C | .23/.15 |
| 5S96 | 1.54/.13 | T L E E M M T A C Q G V G G P G C | .26/.15 |

Fig. 8.

| PEPTIDE CONCENTRATION | EIA A492 Values with Sera Containing or not Containing HIV-1 Antibody, by Plastic Type | | | | | |
|---|---|---|---|---|---|---|
| | PLASTIC TYPE 1 | | PLASTIC TYPE 2 | | PLASTIC TYPE 3 | |
| | Free Peptide | Peptide-BSA Conjugate | Free Peptide | Peptide-BSA Conjugate | Free Peptide | Peptide-BSA Conjugate |
| 2.26µg/ml | | | | | | |
| HIV-1 Antibody Positive | 1.96 | 1.88 | 2.00 | 1.63 | 2.00 | 1.85 |
| HIV-1 Antibody Negative | .15 | .08 | .17 | .10 | .15 | .17 |
| Ratio | 13.1 | 23.5 | 11.8 | 16.3 | 13.3 | 10.9 |
| 0.23µg/ml | | | | | | |
| HIV-1 Antibody Positive | .52 | 1.21 | .45 | .95 | 1.51 | 1.88 |
| HIV-1 Antibody Negative | .06 | .06 | .07 | .09 | .14 | .13 |
| Ratio | 8.7 | 20.2 | 6.4 | 10.6 | 10.8 | 14.5 |
| 0.057µg/ml | | | | | | |
| HIV-1 Antibody Positive | 0.17 | 0.46 | 0.17 | 0.35 | 0.57 | 1.35 |
| HIV-1 Antibody Negative | .06 | .06 | .07 | .07 | .15 | .13 |
| Ratio | 2.8 | 7.7 | 2.4 | 5 | 3.8 | 10.4 |

*Fig. 9.*

| Peptide # | Natural (N) OR Unnatural (U) | Sequence | A492 of 8 Positive Sera median (range) | A492 OF 12 Negative Sera median (range) |
|---|---|---|---|---|
| 2S24 | N | D Q A R L N S W G C A F R Q V C | 1.46 (1.13–1.65) | .12 (.10–.17) |
| 2S25 | N | A R L N S W G C A F R Q V C H G C | 1.19 (1.08–1.58) | .11 (.09–.16) |
| 2S27 | N | S W G C A F R Q V C H G T T V P G C | 1.02 (.75–1.31) | .11 (.09–.15) |
| 5S84 | N | S W G C A F R Q V C H G T T V P G C | 0.96 (.84–1.40) | .10 (.09–.15) |
| 5S85 | N | [A] W G C A F R Q V C H G T T V P G C | 1.37 (1.19–1.71) | .11 (.09–.15) |
| 5S86 | N | S W G C A F R Q V C H G T [S] V P G C | 1.45 (1.18–1.58) | .11 (.09–.16) |
| 5S88 | U | S W G C A [Y] R Q V C H G T T V P G C | 0.64 (.26–1.25) | .11 (.09–.17) |
| 5S90 | U | S W G C A F [H] Q V C H G T T V P G C | 1.32 (1.00–1.40) | .12 (.09–.16) |
| 5S91 | U | S W G C A F [K] Q V C H G T T V P G C | 1.02 (.91–1.30) | .12 (.10–.16) |
| 5S92 | U | S W G C A F R [N] V C H G T T V P G C | 1.39 (1.27–1.78) | .13 (.11–.17) |

*Fig. 12.*

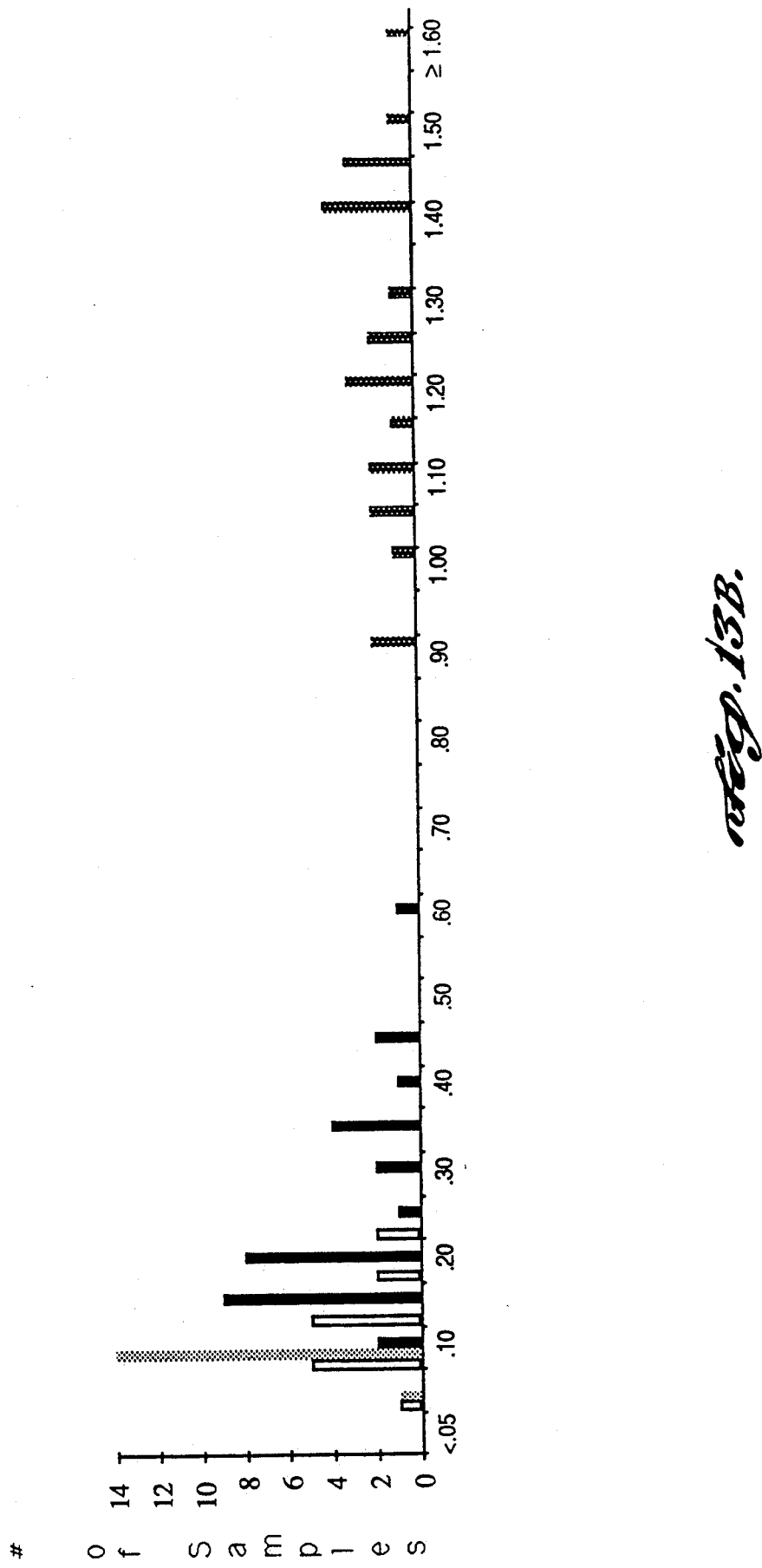

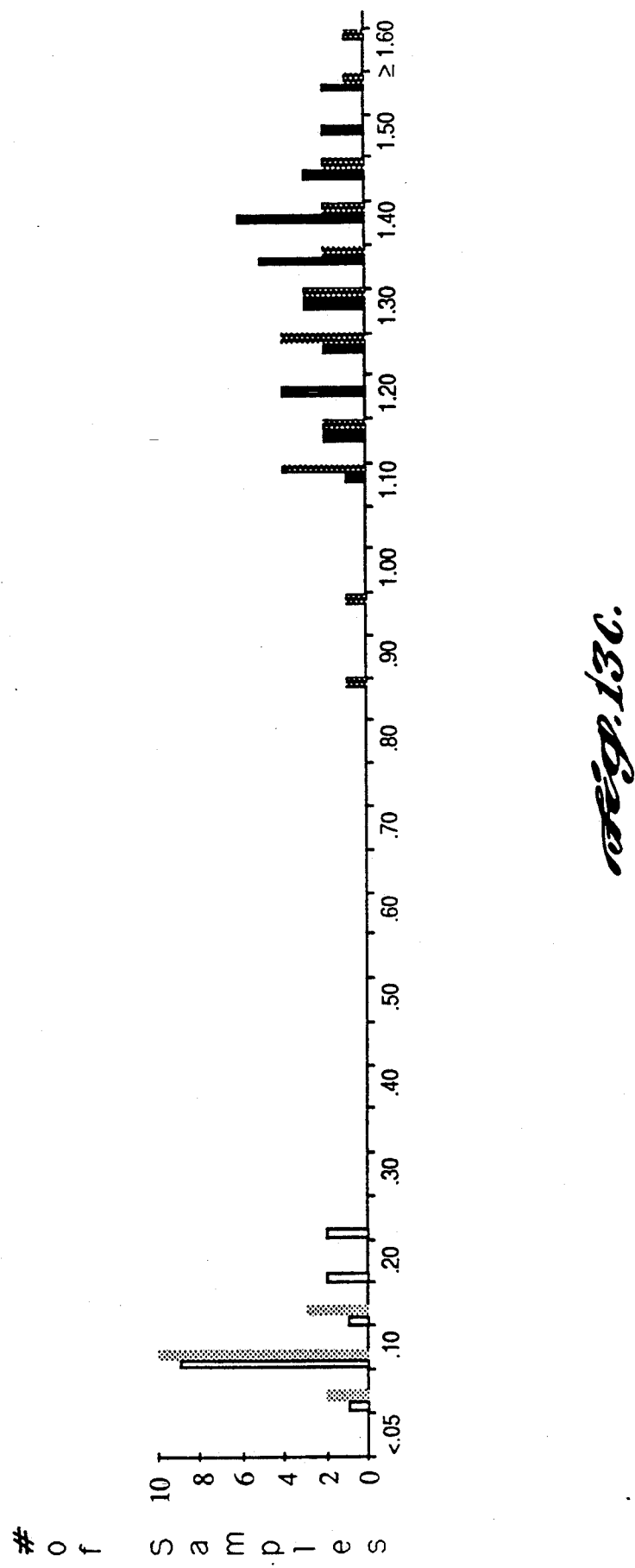

SYNTHETIC HIV-LIKE PEPTIDES THEIR COMPOSITIONS AND USES

This application is a continuation application based on prior copending application Ser. No. 07/840,641, filed on Feb. 24, 1992, which is a continuation of application Ser. No. 07/287,412, filed Dec. 20, 1988, both now abandoned.

FIELD OF THE INVENTION

This invention relates to synthetic peptides having the antibody binding characteristics of Human Immunodeficiency Virus ("HIV") antigens. More particularly, this invention is directed to the discovery that certain sequence variants of natural HIV peptides provide reagents that are equal to or superior to the natural sequence peptides, when used alone or chemically linked to carrier proteins and employed in immunoassays for the detection of HIV antibodies. This invention further relates to methods of use of synthetic peptides and/or peptide-protein conjugates in diagnostic assays that permit rapid visual detection of antibodies to HIV without requiring instrumentation.

BACKGROUND OF THE INVENTION

Human Immunodeficiency Virus Type 1 ("HIV-1") was identified as an etiological agent of Acquired Immune Deficiency Syndrome ("AIDS") in 1983 (Barré-Sinoussi et al., *Science* 220: 868–871, 1983) and 1984 (Gallo et al., Science 224: 500–503, 1984). Human Immunodeficiency Virus Type 2 ("HIV-2") was identified in 1986 and is an important cause of AIDS in Central and West Africa (Clavel et al., *Science* 233: 343–346, 1986) with some reported cases in Europe (Bruckner et al., *Lancet i:* 223, 1987; Saimot et al, *Lancet i:* 688, 1988) and the USA (*New Jersey MMWR* 87: 33–35, 1988).

The two retroviruses display rapid mutation (Hahn et al., *Science* 232: 1548–1553, 1986; Wen-Hsiung et al., *Molec Biol Evol* 5(4): 313–330, 1988; Saag et al., *Nature* 334: 440–444, 1988) and genetic polymorphism with more than 13 strains of HIV-1 and 4 strains of HIV-2 characterized by DNA sequencing (Myers et al., *Human Retroviruses and AIDS*, 1988. *A compilation of nucleic acid and amino acid sequences*. Los Alamos National Laboratory, Los Alamos, N. Mex. 87545, USA).

Tests for HIV infection currently licensed for use in the United States by the United States Food and Drug Administration ("USFDA") employ disrupted HIV-1 virus as the antigen (Petricciani et al., *Ann Int Med* 103: 726–729, 1985; Osterholm et al., *New Engl J Med* 312: 1185–1188, 1985) and are based upon the observation that HIV-1 proteins within these antigen preparations detect antibody as an indirect measure of infection (Allan et al., *Science* 228: 1091–1094, 1985; Barin et al., *Science* 228: 1094–1096, 1985; and Wain-Hopson et al., *Cell* 40: 9–17, 1985). These tests have been helpful in screening blood for HIV-1 contamination and diagnosing exposure to the AIDS virus, but remain limited in sensitivity when a single HIV-1 isolate is used as source of antigen (for example BH8 isolate, U.S. Pat. No. 4,520,113) since HIV displays rapid mutation and multiple genetic variants as noted above and antigenic variants exist (Looney et al., *Science* 241: 357–359, 1988; Palker et al., *Proc Nat'l Acad Sci USA* 85: 1932–1936, 1988). Insensitivity may also result from poor preservation of the immunodominant regions of the HIV gp41 envelope protein in current licensed assay kits that employ viral lysates as the antigen source (Steckelberg and Cockerill, *Mayo Clinic Proc* 63: 377–380, 1988). Further, since current kits employ only HIV-1 protein markers, it is estimated that 75% or more of HIV-2 infections will not be detected (Clavel et al., *New Engl J Med* 316: 1180–1185, 1987).

Tests for HIV infection based upon whole virus lysates as the antigen source have significant deficiencies with regard to specificity. The virus must be grown in cell cultures. HLA and other cell culture contaminants within the antigen may be responsible for false positivity (Eisenstaedt et al., *Am J Public Health* 78: 450–454, 1988; Goedest *Ann Int Med* 105: 609–610, 1988). In populations with a low prevalence of HIV infections, less than 1 in 10 persons who are repeatedly positive with the current tests may actually be infected with HIV (Osterholm et al., *New Engl J Med* 312: 1185–1188, 1985).

Related to the inadequate sensitivity and specificity of many current tests is the ability of a test to discriminate between positive and negative samples. Ward et al., *JAMA* 256: 357–361, 1986, found that over half of the positive results obtained with one test were just above the positive/negative cut-off value. An optimal test would show large differences between positives and negatives for nearly all samples, thereby decreasing the likelihood of false positive test results.

Subsequent refinements in HIV testing, not yet licensed by the USFDA for use within the United States, have employed HIV protein produced by recombinant DNA techniques (Thorn et al., *J Clin Microbiol* 25: 12070–1212, 1987; Burke et al., *Ann Int Med* 106: 671–676, 1987; Dawson et al., *J Infect Dis* 157: 149–157, 1988; and Beltz, et al., U.S. Pat. No. 4,753,873), synthetic peptides related to HIV proteins (Rosen et al., P.C.T. Application Publication No. WO87/06005; Wang et al., *Proc Nat'l Acad Sci USA* 86: 6159–6163, 1986; U.S. Pat. No. 4,735,896; Cosand, U.S. Pat. No. 4,629,783; Smith et al., *J Clin Microbiol* 25: 1498–1504, 1987; and Gnann et al., *J Infect Dis* 156: 261–267, 1987), or a combination of factors (Leslie et al., *Vox Sang* 54: 84–91, 1988). Nonspecificity due to tissue culture contaminants is obviated when either recombinant proteins or synthetic peptides are used as the antigen source, and neither antigen source requires exposure to HIV during the manufacturing process. Synthetic peptides additionally allow standardized antigen production by purely chemical means, and avoid nonspecificity resulting from contaminating proteins of Escherichia coli or other hosts employed to manufacture the HIV protein fragments produced by genetic engineering methods. New peptides may also be quickly incorporated into a manufacturing process if necessitated by mutations of HIV-1 or HIV-2 that affect antigenicity of peptides employed in the diagnostic test. These refinements produce improved tests for antibody to HIV-1, but significant difficulties remain with respect to further improvements in sensitivity and specificity, detection of HIV-2 infections, and adaption of these reagents to rapid simple assays for discrimination between positive and negative samples.

SUMMARY OF THE INVENTION

It has now been determined that these and other problems present in the art may be overcome, and that improved assay results in determining the presence or amount of antibodies to HIV-1 or HIV-2 proteins in a test sample may be obtained by the use of an immunospecific reagent comprising at least one synthetic peptide conjugated through its C-terminus to a carrier protein. Synthetic peptides useful in the immunospecific reagent may be natural or unnatural peptides having the immunoreactive specificity of the p24 or gp41 proteins of HIV-1 or the gp32 protein of HIV-2. The immunospecific reagents of the invention are used by contacting a fluid sample, such as blood or serum, with an immunospecific reagent of the invention, and then determining the presence of amount of antibodies bound to the reagent.

Accordingly, in one aspect of the invention, it has been determined that peptides chemically linked to carrier proteins provide higher positive/negative test ratios and better discrimination between positive and negative samples than "free" peptides. In a representative embodiment of this aspect of the invention, peptides are linked to carrier proteins via a cysteine added to their carboxy-termini (C-termini) for use as immunospecific reagents for the detection of antibodies to HIV-1 or HIV-2.

It has also been determined that some natural sequence variants of the reactive peptides that give suitably low levels of reactivity with normal sera provide inadequate sensitivity and low reactivity with 5 to 10 percent of positive sera. Other natural variant peptides from the same region give higher reactivity with positive samples, but unacceptably high reactivity with normal serum, resulting in low positive/negative ratios, and poor discrimination between those samples containing, and those not containing, antibody to HIV. No natural peptides have been found that meet all desirable criteria for detection of antibodies to HIV-1.

In another aspect of the invention, unnatural sequence variants of natural HIV-1 and HIV-2 peptides are provided that retain high levels of reactivity with positive samples, yet show low reactivity with negative samples. The carrier protein-linked chemical conjugates of the preferred unnatural peptides result in higher positive/negative test ratios than previously tested natural peptides, and only the chemical conjugates of these peptides with a carrier protein, not free peptides, prove suitable for binding to small particle solid supports in the development of rapid simple assays for detection of HIV-1 antibody. Similar conjugates of both natural and unnatural HIV-2 peptides are suitable for detection of HIV-2 antibody.

In yet another aspect of the invention, immunospecific reagents comprising the synthetic peptides of the invention conjugated to a carrier protein, such as BSA or KLH, may be provided either alone or in kit form for use in immunoassays for antibodies to HIV-1 and HIV-2. A particularly preferred new rapid assay format is provided requiring less than 15 minutes to complete, and providing a simple visual end point to detect HIV-1 and/or HIV-2 antibodies.

DEFINITIONS

Several terms and abbreviations commonly utilized in immunochemistry and peptide chemistry appear in the following description and claims. The following definitions are included for clarification.

The term "peptide", as used herein, is a linear sequence portion of a protein comprised of amino acids. The peptides of the present invention are typically about 5 to about 22 amino acids in length. A "natural" peptide or sequence variant means one of the peptide sequence variants that has been isolated from natural sources and previously reported in the literature—currently, 13 sequence variants of HIV-1 have been reported. "Unnatural" peptide or sequence variant means an amino acid sequence that varies from any currently known and reported natural sequence.

The term "antigenic domain" or "epitope" means a region within a protein or peptide, generally about 6 to about 11 amino acids in length, that is capable of specifically interacting with and binding to an antibody.

The following acronyms used herein have the meanings set forth below:

EIA = Enzyme Immuno Assay
ELISA = Enzyme Linked Immuno Sorbent Assay
HIV = Human Immunodeficiency Virus
HIV-1 or HIV-2 (Types 1 and 2 of HIV)
SIV = Simian Immunodeficiency Virus
KLH = Keyhole Limpet Hemocyanin
BSA = Bovine Serum Albumin
(S)MBS = (Sulfo)Maleimidobenzoyl-N-hydroxysuccinimide ester
(Sulfo)SMCC = (Sulfo)Succinimidyl-4-(N-maleimidomethyl)cyclohexane-1-carboxylate
SPDP = N-Succinimidyl-3-(2-pyridyldithio)propionate
p24 Protein = the middle proteolytic fragment of the protein product of the GAG gene of HIV-1
gp41 and gp32 = the transmembrane portion proteolytic fragment of the protein product of the ENV gene of HIV-1 and HIV-2, respectively
AA = amino acid.

The following single letter amino acid codes are used to define specific amino acids:

alanine = A
arginine = R
asparagine = N
aspartic acid = D
cysteine = C
glutamic acid = E
glutamine = Q
glycine = G
histidine = H
isoleucine = I
leucine = L
lysine = K
methionine = M
phenylalanine = F
proline = P
serine = S
threonine = T
tryptophan = W
tyrosine = T
valine = V.

Unless otherwise indicated, all amino acids are natural L amino acids.

BRIEF DESCRIPTION OF THE DRAWINGS AND FIGURES

FIG. 1 shows AA sequences of overlapping peptides of the gp41 protein of HIV-1, isolate HXB2, and the immunoreactivity of these peptides when tested as peptide-protein conjugates against pools of human serum either containing (HIV+) or not containing (HIV−) antibody to HIV-1;

FIG. 2 shows AA sequences of unnatural variants of peptide 2S09, the peptide shown in FIG. 1 to have high immunoreactivity when conjugated to protein. Antigenicity of each unnatural peptide is indicated by its ability as a free peptide to inhibit binding of HIV-1 antibodies to a BSA conjugate of peptide 2S09. Unnatural AA's are highlighted except for the unnatural glycine (G) and cysteine (C) added to the carboxyterminus of each peptide to facilitate coupling to carrier protein;

FIG. 3 shows AA sequences of additional natural and unnatural variants of peptide 2S09. Antigenicity of each peptide is indicated by its ability as a free peptide to inhibit binding of HIV-1 antibodies to a BSA conjugate of either 2S09 or peptide 5S67, a natural sequence variant reported in HIV-1 isolates from Zaire (Gnann et al., Science 237:1346–1349, 1987; and Alizon et al., Cell 46:36, 1986). Each peptide contains an unnatural carboxyterminal GC, and additional variations in AA sequence from peptide 2S09 are highlighted;

FIG. 4 shows the immunoreactivity of each of the peptides found most antigenic as free peptides in FIGS. 2 and 3, when used as a BSA conjugate to directly bind HIV-1 antibodies. AA variants of peptide 2S09 are highlighted and each peptide contains a carboxyterminal GC to facilitate its coupling to BSA;

FIG. 5 shows AA sequences of overlapping peptides of the gp32 protein of HIV-2, isolate ROD, which are nearly identical to SIV AA sequences in this region. The immunoreactivity of these peptides was determined using peptide-protein conjugates tested against pools of macaque serum either containing (SIV+) or not containing (SIV−) antibody to SIV/HIV-2;

Figure 10A:
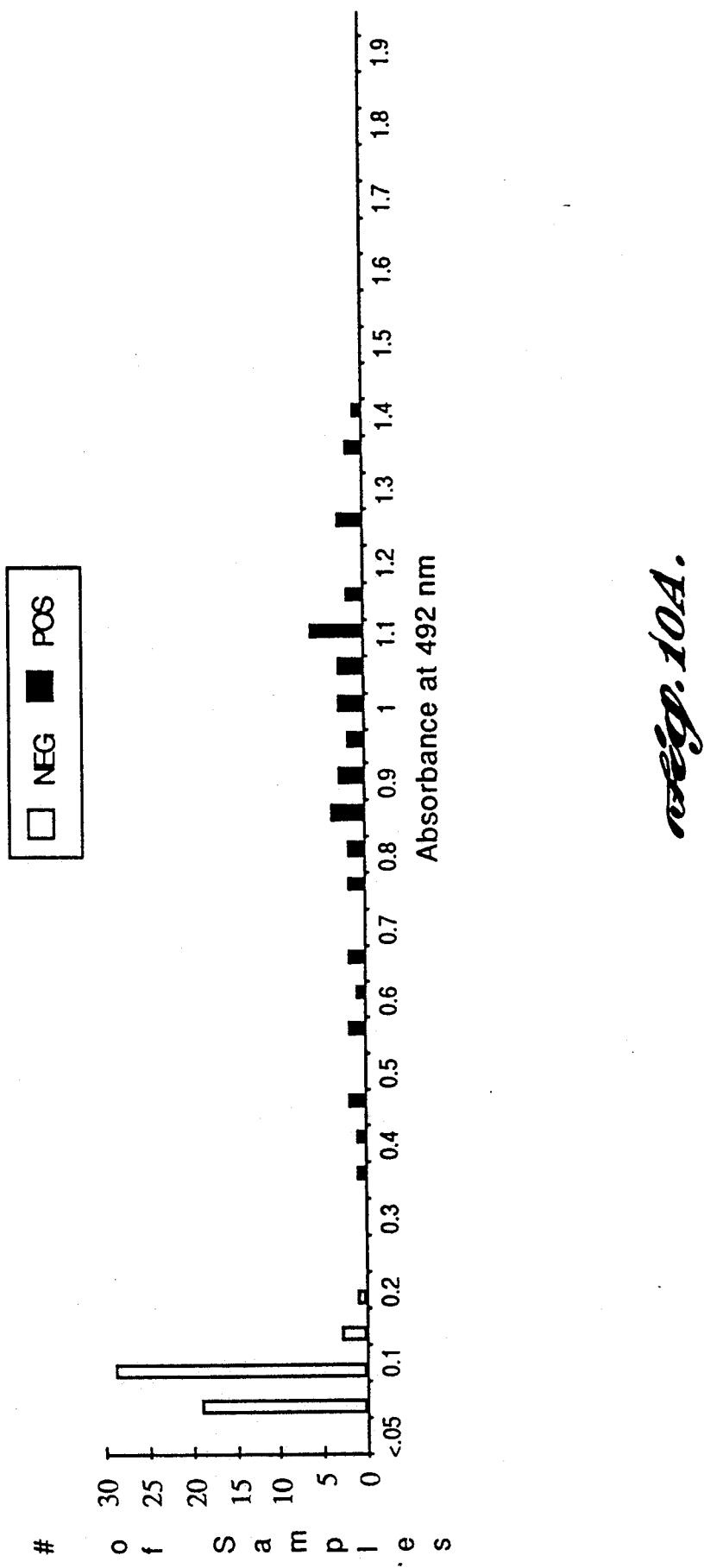

FIG. 6 shows the AA sequences of natural and unnatural variants of peptide 2S27, a peptide shown in FIG. 5 to have high immunoreactivity. Antigenicity of each peptide is indicated by its ability as a free peptide to inhibit binding of SIV/HIV-2 antibodies to a BSA conjugate of peptide 2S27. Unnatural AA's are highlighted and each peptide contains a carboxyterminal GC to facilitate its coupling to BSA;

FIG. 7 shows the immunoreactivity of each of the peptides shown to be most antigenic as free peptides in FIG. 6, when used as a BSA conjugate to directly bind SIV/HIV-2 antibodies. AA variants of peptide 2S27 are highlighted. Each peptide contains a carboxyterminal C to facilitate its chemical linkage to BSA, and most contain a penultimate G spacer;

FIG. 8 shows AA sequences of overlapping peptides of HIV-1 p24 protein, and the immunoreactivity of these peptides when pooled and tested as peptide-protein conjugates against human serum either containing (HIV+) or not containing (HIV−) antibodies to HIV-1. Different groups of peptides were initially conjugated to BSA as indicated and the conjugates of each pool were first tested. Individual peptide conjugates to BSA were prepared only from those peptides within a pool that showed reactivity;

FIG. 9 shows the immunoreactivity of unnatural peptide 4S36 when coated either as a free peptide, or as the same amount of peptide chemically linked to BSA, to 3 different polystyrene EIA microtiter plates. Note that the highest positive/negative ratios (≧20), and greatest discrimination between positive and negative samples, was achieved only with the BSA-peptide conjugate and with plastic having low reactivity with normal human sera (plastic type 1);

FIG. 10A shows the immunoreactivity of Peptide-KLH conjugate of natural peptides 2S06 and 2S09 when tested by EIA with 94 human sera, 42 of which contained, and 52 of which did not contain, antibodies to HIV-1;

FIG. 10B shows the immunoreactivity of peptide-BSA conjugate of natural peptide 2S09 when tested by EIA with 184 human sera, 98 of which contained and 86 of which did not contain antibodies to HIV-1;

FIG. 10C shows the immunoreactivity of peptide-BSA conjugate of natural peptide 5S67 when tested by EIA with 185 human sera, 98 of which contained and 87 of which did not contain antibodies to HIV-1;

FIG. 11A shows the immunoreactivity of peptide-BSA conjugate of unnatural peptide 4S36 when tested by EIA with 183 human sera, 98 of which contained and 85 of which did not contain antibodies to HIV-1;

FIG. 11B shows the immunoreactivity of peptide-BSA conjugate of unnatural peptide 5S76 when tested by EIA with 185 human sera, 98 of which contained and 87 of which did not contain antibodies to HIV-1;

FIG. 11C shows the immunoreactivity of combined peptide-BSA conjugates of unnatural peptides 4S36 and 5S76 when tested by EIA with 183 human sera, 98 of which contained and 85 of which did not contain antibodies to HIV-1;

FIG. 12 shows the immunoreactivity of peptide-BSA conjugates of natural peptides 2S24, 2S25, 2S27, 5S84, 5S85, and 5S86, and unnatural peptides 5S88, 5S90, 5S91, and 5S92 when tested by EIA with macaque sera, 7 of which contained and 13 of which did not contain antibodies to HIV-2;

FIG. 13 shows the separate immunoreactivities of the HIV-1 (FIG. 13A), HIV-2 (FIG. 13B) and combined HIV-1 plus HIV-2 EIA (FIG. 13C) tests with 30 HIV-1 antibody positive, 23 HIV-2/SIV antibody positive, 15 human sera devoid of antibody to HIV-1, and 15 macaque sera without antibody to SIV/HIV-2. All peptides were utilized C-terminally conjugated to BSA. The HIV-1 plates were coated with conjugates of unnatural peptides 4S36 and 5S76. The HIV-2 plates were coated with peptides 2S24 and 5S86, and the combined HIV-1 plus HIV-2 plates were coated with 4S36 (HIV-1) and 2S24 plus 5S86 (HIV-2);

FIG. 14 is a top view of a rapid test device of the invention; and

FIG. 15 is an exploded side view of the rapid test device of FIG. 14.

DESCRIPTION OF THE SPECIFIC EMBODIMENTS

In accordance with one aspect of the invention, the presence or amount of antibodies to HIV-1 or HIV-2 in a fluid sample, such as a blood or serum sample, is determined by contacting the fluid sample with an immunospecific reagent comprising at least one synthetic peptide conjugated through its C-terminus to a carrier protein and having an immunoreactive specificity characteristic of the antigenic domains of the p24 or gp41 proteins of HIV-1 or the gp32 protein of HIV-2, and then determining the presence or amount of antibodies bound to the immunospecific reagent.

Representative peptides useful for C-terminus conjugation to a carrier protein in the practice of the invention are preferably synthetic peptides having amino acid sequences representative of the antigenic domain of naturally occurring HIV-1 and HIV-2 proteins (for sequences of naturally occurring HIV-1 and HIV-2 proteins, see Myers et al., *Human Retroviruses and AIDS*, 1988, *A compilation of nucleic acid and amino acid sequences*, Los Alamos National Laboratory, Los Alamos, N. Mex., 87545, USA). Other peptides of the invention include unnatural synthetic peptides having an immunoreactive specificity characteristic of the antigenic domains of HIV-1 or HIV-2, which are more fully described herein. The peptides may be chemically synthesized, such as by using a modification of standard Merrifield solid phase synthesis technology, known as Simultaneous Multiple Peptide Synthesis (SMPS), that allows synthesis of approximately 70-100 peptides at once (see U.S. Pat. No. 4,631,211). Following this procedure, peptides were synthesized representing all primary and secondary structure epitopes or antigenic domains contained within peptides of 11 or fewer amino acids, and representing all of the p24 protein encoded by the gag gene of HIV-1, and portions of the transmembrane glycoprotein encoded by the env genes of HIV-1 and HIV-2. The initial sequence used for HIV-1 was that of the HIVHXB2 clone, and for HIV-2 was that of the HIVROD clone (Myers et al., supra) but once immunodominant regions of the env transmembrane glycoprotein were identified, all of the known common natural sequence variants of the immunoreactive region, as well as many unnatural sequence variants of this region, were synthesized as described herein.

Representative peptides of the invention comprise from about 5 to about 22 amino acids, preferably from about 11 to about 20 amino acids, and more preferably from about 15 to about 17 amino acids. The peptides preferably comprise less than 20 amino acids in length, to avoid the rigid secondary structure assumed by some longer molecules. Such secondary structure rigidity may interfere with the peptides adapting their shape to the antigen-binding site of the antibodies to HIV gp41, gp32 or p24 found in infected patients. The lower immunoreactivity of some peptides generally described in the art, but without a GC C-terminus tail as shown in FIG. 1, such as peptide 4S24 (19 AA's, see Cosand, supra) compared to partially overlapping shorter peptide 2S01 (14 AA's) or of peptide 4S25 (26 AA's, see Cosand and Wang et al., supra, as compared to partially overlapping peptides 2S04 (17 AA's) or 3S36 (17 AA's) may reflect such secondary structure considerations. Polypeptides such as those of the very large protein produced by recombinant DNA methodology (see Beltz et al., U.S. Pat. No. 4,753,873) would be expected to have strong secondary and tertiary structure rigidity that limits accessibility of some epitopes, and contributes to the low immunoreactivity for some antibody positive samples as was observed by Beltz et al. The smaller peptide size employed in the present invention may be expected to be a disadvantage when the peptide is used by itself (not conjugated to a carrier protein), for immunoassays. Such small free peptides may be compromised during the binding process, resulting in lower immunoreactivity. Epitope interference during binding may explain, for example, the observation by Gnann et. al., J Infect Dis 156:261-267, 1987, that 65% of positive samples reacting with a small immunoreactive peptide bound directly to polystyrene gave A492 values of less than 1.0 when tested at a 1:128 dilution. Such epitope interference during binding of unconjugated peptides may also explain the use of longer peptides as the preferred peptides of Rosen et al. (PCT Application WO87/06065) as well as the use of multiple peptides disclosed therein.

In contrast to the foregoing, the immunoreagents of the invention are formed by chemically coupling a small synthetic peptide, as described herein, to a carrier protein prior to use as an immunoreagent. Accordingly, no antigenic peptides are missed due to short peptides not binding to the polystyrene surface of typical assay devices, or to masking of epitopes or steric hindrances introduced by interaction of the short peptide with the plastic surface. Suitable carrier proteins for conjugation to the synthetic peptides of the invention include any naturally occurring or synthetic polypeptide or protein molecules having a molecular weight greater than about 5,000 daltons which are not immunoreactive with a test sample to be analyzed and which do not significantly contribute to or detract from the reactivity of the synthetic peptide. Representative carrier proteins include bovine serum albumin (BSA), keyhold limpet hemocyanin (KLH), human serum albumin, poly-L-lysine, bovine gamma globulin, and other similar polypeptide molecules. Presently preferred carrier proteins include BSA and KLH, with BSA being presently particularly preferred for obtaining optimum assay sensitivity and specificity.

It has been determined that the synthetic peptides of the invention retain a high degree of immunoreactivity when chemically bound via their carboxy-termini (C-termini) to carrier proteins. Conjugation of the peptides to a carrier protein may be accomplished by conventional peptide linkage means using a suitable linking agent, such as p-maleimidobenzoic acid, p-methyldithiobenzoic acid, maleic acid anhydride, succinic acid anhydride, gluteraldehyde, or other similar linking agents. Particularly preferred linking agents include maleimidobenzoyl-N-hydroxysuccinimide ester (MBS), sulfomaleimidobenzoyl-N-hydroxysuccinimide (SMBS), succinimidyl-4-(N-maleimidomethyl) cyclohexane-1-carboxylate (SMCC), sulfosucinimidyl-4-(N-maleimidomethyl) cyclohexane-1-carboxylate (sulfo SMCC), and N-succinimidyl-3-(2-pyridylthio)propionate (SPDP).

To facilitate conjugation to the carrier protein, synthetic peptides of the invention are preferably provided with an amino acid spacer tail located carboxy terminal to the portion of the peptide representing the antigenic domain. Suitable spacer tails function to protect immunoactivity of the antigenic domain upon binding of the peptide to the carrier protein, and to provide a desired terminal amino acid to participate in the conjugation bond. Suitable spacer tails include a peptide segment having from 0 to 4 glycine AA spacers terminating in a cysteine group for conjugation to the carrier protein. In the particularly preferred embodiment described in detail herein, and shown in the drawings, the amino acid spacer tail is represented in the peptides by a C-terminus -GC group, although other spacer tails may be employed for this purpose.

Figure 13A:
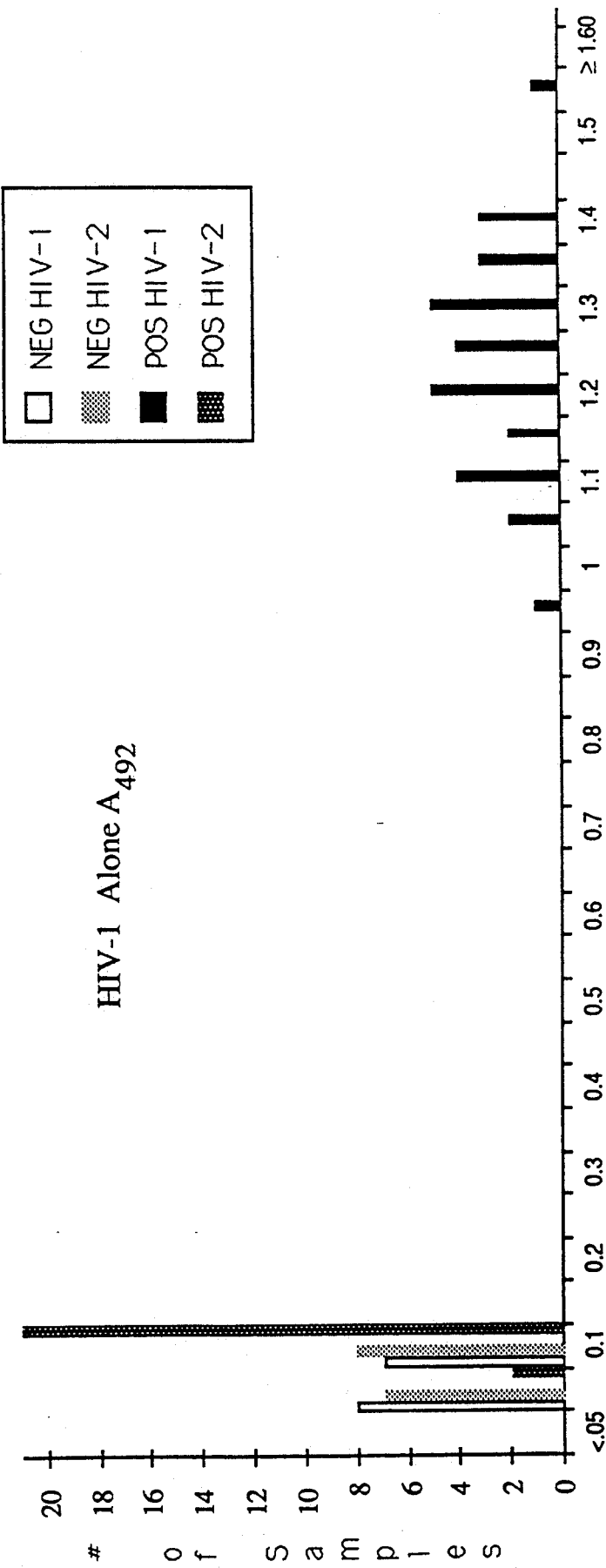
Figure 14:
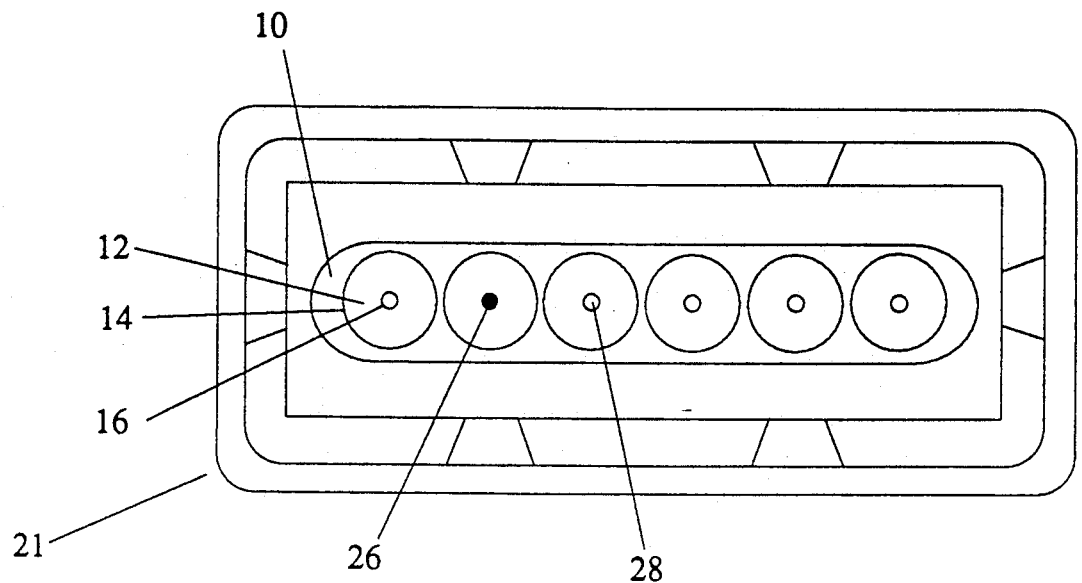

Preferred peptides of the invention were screened by EIA for immunoreactivity against a pool of approximately 50 HIV-1 antibody positive sera, or a pool of approximately 6 HIV-2 antibody positive sera, as well as against pools of sera known to be devoid of antibodies to HIV-1 or HIV-2. By using pools of sera for EIA screening, those peptides to which the highest antibody responses occurred in primates during HIV infection were identified, avoiding mapping epitopes seen by single individuals. Once promising peptide regions were identified (FIGS. 1, 5, 8), optimally immunoreactive peptides were elucidated by additional syntheses (FIGS. 2-4, 6, 7) and the optimized peptides were then screened against a larger number of individual sera (see below, FIGS. 10-13). The best of these optimized peptides, as C-terminal conjugates to BSA, were then utilized to develop rapid visual tests not requiring instrumentation (FIG. 14).

These investigations identified a gp41 natural sequence peptide with the sequence IWGCSGKLICT-TAVPGC (2S09) (underlining signifies extra unnatural amino acids added as a spacer tail to protect immunoactivity and to facilitate coupling) as maximally immunoreactive for detection of antibodies to HIV-1 when bound to carrier protein via cysteine (FIG. 1). In addition three gp32 natural sequence peptides with sequences DQARLNSWGCAFRQVC (2S24), ARLNSW-GCAFRQVCHGC (2S25) and SWGCAFRQVCHTTVPGC (2S27) were identified as maximally immunoreactive for detection of antibodies to HIV-2 when bound to carrier protein via cysteine (FIG. 5). Also identified for the p24 protein was a peptide with the sequence ALGPAATLEEMMTACGC (5S94) that shows significant immunoreactivity when chemically linked to carrier protein via cysteine (FIG. 8).

The immunoreactive region for HIV-1 represented by peptides of the invention is located C-terminal to the regions identified by Wang et al., U.S. Pat. No. 4,735,896, and by Cosand, U.S. Pat. No. 4,679,783 (FIG. 1). The immunoreactive peptide of Wang, with the sequence RILAVERYLKDQQLLGIWGCS, and the immunoreactive peptides of Cosand, with the sequences IKQLQARILAVERYLKDQQ (4S24) and RILAVE-RYLKDQQLLGIWGCSGKLIC (4S25), differ from the peptides which are the subject of this invention as follows. Shorter peptides AVERYLKDQQLLGC (2S01), ERYLKDQQLLGIWGC (2S02), and YLKDQQLLGIWGCSGC (2S03) of the invention, which cover 18/21 of the total Wang peptide, and all its C-terminus, are significantly less immunoreactive than the immunoreactive peptides of this invention when used as conjugates of a carrier protein chemically coupled to BSA via their C-termini (FIG. 1). The peptide IKQLQARILAVERYLKDQQ (see Cosand, supra) does not overlap the HIV-1 immunoreactive peptides of this invention in any respect, and the much longer peptide RILAVERYLKDQQLLGIWGCSGKLIC (4S25, see Cosand, supra) linked via GC to BSA shows lower or comparable immunoreactivity to several shorter peptides of the invention including KDQQLLGIWGCSGKLGC (2S04), QQLLGIWGCSGKLICGC (3S36), LLGIWGCSG-KLICTTGC (2S06), and LGIWGCSGKLICTTAGC (2S07) when used as C-terminal chemical conjugates with BSA via a GC spacer (FIG. 1). However, the best immunoreactivity is obtained with new peptides of this invention, all of which contain significant sequences not found in either the Wang et al. or Cosand patents. These sequences are C terminal to the Wang and Cosand peptides and are important for maintaining immunoreactivity of peptides when bound via a carboxyterminal GC to carrier proteins such as BSA. The peptides showing this higher reactivity include IWGCSGKLICT-TAVPGC (2S09), GCSGKLICTTAVPWNGC (2S11), CSGKLICTTAVPWNAGC (3S51), SGKLICTTAVPWNASGC (2S13), GKLICTTAVP-WNASWGC (3S55), and KLICTTAVP-WNASWSGC (2S15) (FIG. 1). Some of these natural sequence higher reactivity peptides are similar to those described in Rosen et al. (PCT WO87/06005). However, in contrast to Rosen who used the peptides in unconjugated form, optimal immunoreactivity of these peptides is obtained only when they are used as peptide-carrier protein conjugates, such as when linked to BSA via a glycine-cysteine spacer added to their C-termini (FIGS. 1, 5, 8 and 9). The greatest positive/negative ratios, and best discrimination between samples containing (HIV antibody positive) and those not containing (HIV antibody negative) antibodies to HIV is obtainable only with such conjugates and not with the peptides by themselves (FIG. 9). Furthermore, adaption of these peptides for rapid diagnostic assays is permitted only by the C-terminal peptide-protein conjugates, and peptides by themselves prove unsuitable for either colloidal-gold or EIA formats for a rapid test, as is hereinafter more fully described. (Examples 15-19Table 4).

Having located peptides that retain high performance characteristics for detection of antibodies to HIV when bound via a carboxy-terminal GC to carrier proteins, the most promising of these conjugates were tested against a larger number of serum specimens. These studies indicate that BSA is a superior protein to KLH for preparing peptide-protein conjugates for use in EIA (FIGS. 1, 5, 10 and 11), that more than a single peptide-BSA conjugate is preferred for adequate sensitivity in the detection of antibodies to HIV-1 or to HIV-2 (FIGS. 10-13), and that peptides suitable for HIV-1 detection are unsuitable for detection of HIV-2 and vice versa (FIG. 13). It has also been confirmed, as shown in Gnann et al. (*Science* 237:1346-1349, 1987) that sequence variants containing histidine substitutions for leucine described for isolates from Zaire are able to detect antibodies to HIV-1 in some sera with low immunoreactivity with HXB2 sequence variant (FIGS. 4 and 10C). However, these histidine containing sequence variants give unacceptably high reactivity with sera containing no antibodies to HIV (FIG. 10C).

No natural sequence variants of the discovered epitope have been found that give optimal assay performance in terms of sensitivity and separation of positive from negative samples, when either single peptides or combinations of peptides bound via their carboxy-termini to BSA or other carrier protein are used as the EIA antigen (FIG. 10). Accordingly, more than 50 unnatural sequence variants of the immunodominant HIV-1 gp41 epitope have been synthesized to identify sequences that retain high immunoreactivity for antibodies to HIV without showing undesirable nonspecific reactivity with sera containing no antibodies to HIV. An important aspect of this invention is the discovery of unnatural sequence variants of both HIV-1 and HIV-2 shown in FIGS. 2-4, 6 7, and 11) that retain high levels of immunoreactivity with antibodies to HIV, and that do not react undesirably with normal human serum devoid of antibodies to HIV (FIG. 11). These highly immunoreactive unnatural sequence variants differ significantly from peptides disclosed in the art. Two of these peptides, 4S36 and 4S76, when used as a conjugate with BSA via their carboxy-termini, provide superior assay performance characteristics, with high levels of sensitivity and specificity, very high levels of discrimination between positive and negative samples (FIG. 11C), and very low reactivity with serum samples found to give false positive reactions with two commercially licensed EIA tests (Example 8, Table 1). This type of assay performance, with no positives giving absorbance values at 492 nm of less than 1.25, and a separation in $A_{492}$ values of between the lowest positive and the highest negative of more than 1.0 absorbance units, is made possible by the combined unnatural peptides described herein used as peptide-BSA conjugates. This type of assay performance is optimal and may be contrasted with the performance of the very large polypeptide produced by recombinant DNA methodology described in U.S. Pat. No. 4,753,873 of Beltz et al., which contains most of the gp120 and gp41 of HIV isolate BH8, including the regions described herein. The separation achieved between positive and negative samples in $A_{490}$ units described in the Beltz et al. patent is only 0.1, and 11% of the positive samples have $A_{492}$ values less than 1.2. The synthetic peptide approach of this invention allows incorporation of several different peptides that represent the entire range of antigenic variation for critical immunodominant regions of the HIV envelope, rather than depending upon a single HIV isolate as in the Beltz et al. patent. Also, via peptide synthesis only the immunodominant regions are included in the antigen used, avoiding nonspecificity that may be introduced by including possible cross-reactive portions of the HIV env gene product, or nonspecificity that may result from contaminating proteins derived from the bacterial host used to produce the recombinant DNA expressed protein.

The immunospecific reagents of the invention may be employed in immunoassays for the detection of antibodies to HIV proteins in sample fluids, such as blood or serum samples, or for the detection of HIV protein antigens. The reagents may be widely used in a variety of assay formats well known to those skilled in the art, including, for example, enzyme-linked immunosorbent assays (ELISA assays), other enzyme immunoassays (EIA assays), radioimmunoassays (RIA assays), immunoradiometric assays (IRMA assays), and other assay formats requiring an immunospecific binding partner. The reagents are preferably employed in assays for the detection of antibodies to HIV proteins wherein a fluid sample to be analyzed is contacted with a reagent of the invention, and the presence or amount of antibodies which bind to the reagent is determined as an indication of the presence or amount of antibodies to HIV present in the sample. Preferably, means are provided for separating reagent/antibody complexes from the sample mixture and detectable labels are employed for detecting the reagent/antibody complexes which are formed. Separation may be achieved by immobilizing the reagents on a solid phase, by filtering the formed complexes from the reaction mixture, or by other means conventional in the art. Suitable solid phases include, without limitation, microtiter plates, glass beads, polystyrene beads, latex beads, microparticles, cellulose matrices, nitrocellulose matrices, silica gels, and other similar solid phase surfaces.

Various labels may also be employed to assist in the detection of reagent/antibody complexes which are formed, as is conventional in the art. Thus, suitable labels include, without limitation, enzymes, radionuclides, luminescent moieties, fluorescent labels, chemiluminescent labels, magnetic particles and directly visible labels, such as colloidal gold.

Tests currently licensed in the United States by the USFDA for detection of antibodies to HIV are EIA tests, which require expensive instrumentation and 2 to 4 hours to complete, and are designed for testing large numbers of sera at once. In many settings, improved detection of antibodies to HIV could be attained if a reliable test were available that was not dependent upon instrumentation, had a simple format and a visual end point, could be performed on a small number of samples, and could be completed in 15 minutes or less. Accordingly, a rapid test format is provided herein by a method and simple device designed for the performance of a visual test on 5 or fewer samples and a control. Two different formats for use of this device are described in Examples 15 and 16 below. In each instance the peptide-protein conjugates of this invention are utilized to accomplish a simple visual test that can be completed in less than 15 minutes. As illustrated in the examples, free peptide is ineffective or less effective for these purposes, whereas the peptide-BSA conjugates perform well. In general, the same peptide-protein combinations that provide the best performance in EIA tests also provide superior performance in the rapid visual tests that are simple to perform.

The above discoveries are intended to include several modifications that would be obvious to those familiar with the art. For example, this invention defines both natural and unnatural peptides that are superior to any of those previously described for detection of antibodies to HIV when linked to BSA via a G (glycine) spacer and a C (cysteine) C-terminal amino acid. However, the discovery that superior assay performance is obtained with such peptide-protein conjugates might also apply to similar conjugates in which: 1) the linking C-terminal amino acid is different, such as methionine, tyrosine, lysine, arginine, glutamic or aspartic acid rather than cysteine; 2) the protein used for conjugation is different, such as bovine gamma globulin, KLH, poly-L-lysine or any other pure polypeptide or protein of 5,000 or larger molecular weight that does not contribute immunoassay reactivity of the conjugate with normal human serum not containing antibodies to HIV; 3) linkers other than those specifically set forth herein are used to accomplish covalent linkage between a thiol, carboxyl, or other group on the C-terminus of the peptide and a similar reactive group on the polypeptide or protein used for conjugation; 4) 0-4 glycine spacers are used for the bridge between the reactive peptide and the C-terminal amino acid; or 5) the C-terminal one to three amino acids of the peptide are modified. However, some of these modifications have been found to provide inferior assay performance compared to the preferred peptide-BSA conjugates described herein. For example, the peptides of the invention are highly reactive when linked to protein carriers via cysteines and their C-termini. These same peptides would not be expected to be optimally immunoreactive if bound via amino groups and their N-termini, since this would result in exposure of a different portion of the peptide for interaction with antibodies. This principle of the importance of peptide orientation has been demonstrated by Dryberg and Oldstone (*J Esp Med* 164:1344–1349, 1986). Indeed, when optimally immunoreactive peptides 4S36 and 5S70 (FIGS. 2–4) are covalently bound via their amino groups to carboxylated latex employing carbodiimides, all immunoreactivity is lost (see Example 16).

The examples below illustrate several different assay and reagent designs, and assay formats for detection of antibodies to HIV, employing the natural and unnatural peptide-protein conjugates defined in this invention. These include use of the conjugates as antigens when bound to polystyrene plastic surfaces for EIA tests, when labelled with colloidal gold for use in a rapid test format and, when bound to latex for use in a rapid EIA format. However, to those familiar with the art, other applications will be readily apparent, and the scope of this invention is meant to include such other possible equivalent uses of the peptide-protein conjugates. For example, the solid surface utilized need not be confined to polystyrene surfaces or latex beads, and might include glass, polypropylene, dextran, nylon, nitrocellulose, gelatin, paper, silical gel, red blood cells, liposomes or the like. Similarly, the peptide-protein conjugates might work equally well as peptide-peptide polymers, and labelling of such conjugates need not be confined to colloidal gold. Alternate methods of labelling the peptide containing polymers might include radioactive labels, enzyme labels, fluorescent labels, antibody labels, liposome labels, free radical labels, or bacteriophage labels.

In addition to their usefulness as diagnostic reagents, the peptide-protein conjugates described herein may be utilized as immunogens, for example to immunize animals to raise polyclonal antibodies to the diagnostic peptide epitope, produce an immune response in mice in preparation for hybridoma technology to prepare monoclonal antibodies to the peptide, and to immunize primates to induce a protective immune response directed at important domains of the HIV proteins contained within the peptides represented. These and other uses of the described HIV peptide-protein conjugates will be apparent to those skilled in the art.

EXAMPLES

The following examples are provided to describe in detail some of the representative, presently preferred methods and materials of the invention. These examples are provided for purposes of illustration of the inventive concepts, and are not intended to limit the scope of the invention as defined by the appended claims.

For all of the immunoassays employing human serum, the serum samples were obtained from the King County Health Department, Seattle, Wash., U.S.A., and each serum had been characterized as positive or negative with respect to antibodies to HIV-1, as determined by testing with the commercially licensed Genetic Systems and or DuPont EIA tests. Serum from rhesus macaque monkeys (Macaca mulatta) was obtained from the University of Washington, Seattle, Wash., U.S.A., and had been characterized by a SIV whole virus lysate EIA as either containing or not containing antibodies to SIV which is nearly identical in sequence to HIV-2 in the region of the peptide epitopes studied.

EXAMPLE 1

Synthesis of Peptides, HF Cleavage of Peptides from Resin, and Characterization of Adequacy of Peptides by HPLC Typically, 72 to 96 peptides were synthesized at once, using a modification of the Merrifield solid phase peptide synthesis methodology known as Simultaneous Multiple Peptide Synthesis (SMPS) and disclosed in U.S. Pat. No. 4,631,211. In this example, 96 separate peptides were synthesized as peptide amides as follows: 100 mg of a 4-methylbenzhydrylamine resin (Colorado Biotechnology Associates, Boulder, Colo., U.S.A.; other resins may be used including PAM or standard Merrifield resin) with a substitution level of approximately 0.6 meq/gm resin was weighed into each of 96 separate 20×25 mm pre-weighed polypropylene bags of 74 micron mesh size sufficient to retain the resin. Each bag was then sealed with an impulse heat sealer (Accu-Seal Corporation, San Diego, Calif., U.S.A.), and a numbered label of India ink was also heat-sealed into the bag to allow identification of each "T-bag" throughout the synthesis procedure. The prepared packets were thoroughly washed by shaking in methylene chloride to remove any resin fines and to identify any improperly sealed bags, and then dried and weighed to determine residual resin weight and starting weight of each bag for the synthesis. Amino acids used in the synthesis were obtained from Omni Biochemical (San Diego, Calif., U.S.A.; amino acids from other sources may also be used, such as those which are commercially available from Applied Biosystems Inc., Foster City, Calif., U.S.A., Peninsula Laboratories, Belmont, Calif., U.S.A., and Bachem, Torrence, Calif., U.S.A.) and were N-alphaamino protected by a tertiary butyloxycarbonyl (t-Boc) group. Some amino acids additionally contained side chain protecting groups, such as benzyl for aspartic acid, glutamic acid, serine, and threonine; p-methylbenzyl for cysteine; dinitrophenyl for histidine; ortho-chloro-benzyloxycarbonyl for lysine; tosyl for arginine; and ortho-bromo-benzyloxycarbonyl for tyrosine. The t-Boc protected amino acids alanine, phenylalanine, tryptophan, glycine, isoleucine, leucine, asparagine, glutamine, proline, and valine were used without side chain protection.

In each step of the SMPS synthesis, complete interaction of the solvent and reactants with the resin and growing peptide chain was assured by vigorous shaking on a mechanical shaker, and all of the solvent from the preceding step was removed prior to addition of the solvent for the subsequent step. The resin containing packets were washed for 1 minute in methylene chloride, followed by three 2 minute washes in 5% diisopropylethylamine (DIEA) in methylene chloride, and two subsequent one minute washes in methylene chloride. The resin packets were then sorted for placement into a container appropriate for the individual amino acid desired as the carboxy-terminal amino acids. All of the peptides in this group of 96 contained a C-terminal cysteine, followed by a glycine spacer, so all of the packets were handled together for the first two amino acids. The amino acids were solubilized in methylene chloride, or 90% methylene chloride plus 10% dimethylformamide (DMF) at 0.2M concentration, and added to the appropriate reaction bottle in an 8 fold molar excess over resin capacity. Each amino acid solution was activated just prior to use by 2 ml per resin packet of activator solution consisting of 0.2M diisopropylcarbodiimide in methylene chloride. The coupling of the appropriate amino acid to each resin packet was accomplished during one hour on the shaker, and followed by one 30 second wash with DMF to remove disopropylurea and any remaining amino acid, and one 30 second wash with methylene chloride. All of the resin packets were then combined in the original large reaction bottle and washed twice with methylene chloride for one minute each time. The coupled amino acid on each resin was then deprotected to remove the N-alpha-t-Boc group by treatment with 55% trifluoroacetic acid (TFA), 45% methylene chloride for 30 minutes, followed by a one minute wash with methylene chloride, two one minute washes with isopropanol to shrink the resin and remove any remaining TFA, and two one minute methylene chloride washes. The alpha amino salts were then neutralized with ice-cold 5% DIEA-$CH_2Cl_2 \times 3$, followed by washing with methylene chloride twice. Coupling of protected amino acids, washing, deprotection, etc., were repeated until all desired amino acids were added to the peptide chain. At this point the N-alpha-t-Boc groups were removed from each peptide by treatment with 55% TFA/45% $CH_2Cl_2$ for 30 minutes, followed by one $CH_2Cl_2$ wash×1 minute, two isopropanol washes of 1 minute each, two one minute washes with $CH_2Cl_2$, and drying in the lyophilizer. The fully dried resin packets were weighed and an estimate of coupling completion was made by comparing the weight gain with theoretical. Any peptides containing histidine were further treated with 0.5M thiophenol to remove the dinitrophenyl side chain protective group. The thiophenol was added in 3 separate amounts each for one hour, followed by 10 washes with DMF, followed by 10 washes each of alternating isopropanol or methylene chloride. The thiophenol treated resin was then completely dried in the lyophilizer. For peptides that were not of high purity as evaluated by HPLC after HF cleavage, extraction and lyophilization, resynthesis was accompanied by monitoring of coupling completion with picric acid. Following the coupling steps, the resin packet was treated with a 0.05M concentration of picric acid in methylene chloride. Visual inspection for yellow color gave a qualitative estimation of coupling completion, which was quantitated by eluting the picric acid from the resin with 5% DIEA in methylene chloride and monitored at 358 nm. This method detected as little as 0.5% unreacted amine on the resin.

The peptides were cleaved from their resins and side chain protective groups were removed simultaneously in an HF cleavage apparatus (Multiple Peptide Systems, La Jolla, Calif. U.S.A.) that allowed simultaneous treatment of 24 separate peptides. The standard high HF procedure was utilized (90% v/v anhydrous Hydrogen Fluoride (HF), 10% v/v anisole, 0° C., 60 minutes). Following cleavage, the HF was removed by a combination of $N_2$ flow and vacuum. The resin packets were washed three times with ether to remove carbonium ion scavenger, and then extracted with 15% acetic acid followed by 45% acetic acid. An aliquot of the 15% acetic acid extracted peptide was frozen for analysis by HPLC and the remaining extracts were pooled and lyophilized. Lyophilized peptides were analyzed by reverse phase chromatography using a Synchropak C-4 column (Supelco, Bellefonte, Pa., U.S.A.) eluted with a linear gradient of 0 to 30% acetonitrile at 0.33%/min plus 0.1% trifluoroacetic acid at a flow rate of 1 ml/min, using a Beckman HPLC Model 421 (Beckman Instruments, Palo Alto, Calif. U.S.A.) and Hewlett Packard diode-array detector Model 1040A (Hewlett Packard, Palo Alto, Calif., U.S.A.) Peptides considered to be of acceptable purity showed a single peak comprising $\geq$90% of the chromatogram. These peptides were chosen for further evaluation as an antigen in an immunoassay to detect antibodies to HIV. The foregoing procedure was repeated to synthesize each of the synthetic peptides shown in FIGS. 1-8.

EXAMPLE 2

Chemical coupling of synthetic peptides to KLH or BSA

The synthetic peptides of FIGS. 1-8 were reduced with 10 mM DTT, or with immobilized DTT (Reductacryl, Calbiochem, San Diego, Calif., U.S.A., 10 mg Reductacryl per mg peptide) overnight at 4° C., pH8 in 10 mM borate or other buffers depending upon peptide solubility, with gentle mixing. KLH was dissolved at a concentration of 10-30 mg/ml in 10 mM phosphate buffer pH 7.2., and BSA was dissolved at a concentration of 20-80 mg/ml for treatment with heterobifunctional linkers MBS (m-Maleimidobenzoyl-N-hydroxysuccinimide ester), SPDP [N-Succinimidyl 3-(2 pyridyldithio)propionate], or Sulfo-SMCC [Sulfo-Succinimidyl 4(N-maleimidomethyl)-cyclohexane-1-carboxylate]. The heterobifunctional linkers were added to the protein solutions in a molar excess of linker to BSA of 100, or of linker to KLH of 1000. MBS was dissolved in DMF at 10 mg/ml, SPDP was dissolved in absolute ethanol at 10 mg/ml and each of these was added dropwise with mixing into the protein solution, whereas the Sulfo-SMCC dry powder was dissolved into the protein solution. Each protein-linker mixture was reacted at room temperature for 15 minutes to 1 hour and then free linker was separated from BSA-linker or KLH-linker by gel chromatography with Sephadex G25 using 50 mM phosphate, pH 6 for KLH-MBS, 10 mM acetate, 100 mM NaCl, pH 4.6 for BSA-SPDP, or 100 mM phosphate, 1 mM EDTA, pH 6.5 for BSA-SMCC. The reduced peptides were separated from DTT by Sephadex G10 column chromatography when soluble DTT was used, or by centrifugation followed by filtration through a 0.22 micron filter when Reductacryl was used. Reduced peptides were combined with linker treated KLH or BSA in molar ratios of 100-1000 peptide/KLH-MBS, 1-50 peptide/BSA-SMCC, and 0.1-10 peptide/BSA-SPDP. Each reduced peptide was added to the linker-treated protein with mixing, overlayed with $N_2$, and then mixed gently at room temperature for one hour, and then overnight at 4° C. The SMCC-BSA conjugates were further treated with a 1 mM final concentration of mercaptoethylamine for 4 hours, and then dialyzed overnight against 100 volumes of buffer (20 mM phosphate, 1 mM EDTA, 0.05% sodium azide, pH 6.5) at 4° C. All other conjugates were adjusted to a final concentration of sodium azide of 0.05%. Optimal molar ratios of peptide/protein for the conjugates were determined by solubility and antigenicity (as evaluated by EIA). For example, the best ratios were found to be approximately 1:1 (SPDP-BSA), 10:1 (SMCC-BSA), and 100:1 (MBS-KLH).

EXAMPLE 3

Immunoassays to evaluate the Immunoreactivity of Free Peptides or Peptide-Protein Conjugates The free peptides or peptide-protein conjugates of FIGS. 1-13 were initially screened for immunoreactivity by coating each well of polystyrene microtiter EIA plates (Costar, Cambridge, Mass., U.S.A.) with 0.2 ml amounts of concentrations of 5-50 micrograms/ml peptide in Tris buffer, 10 mM, pH 8.0, at 4° C. overnight. Peptides or peptide-protein conjugates showing immunoreactivity by EIA were then further diluted for coating to determine the minimal concentrations required that allowed maximal immunoreactivity with antibodies to HIV, and minimal nonspecific reactivity with normal sera. The EIA tests were performed as follows: The coating solution was removed from each well and the wells were blocked at 37° C. for 30 minutes with a solution of 50 mM phosphate, 100 mM NaCl, pH 7.4, 1% BSA, 0.5% gelatin. The wells were then aspirated dry with a microtiter plate washer and washed 3 times with a solution of 50 mM phosphate, 100 mM NaCl, 0.05% Tween 20, pH 7.4 (PBST). A 1:101 dilution (in PBST with 1% BSA, 1% NRS) of the primate serum to be tested was then added as 0.2 ml to each washed well and the plates were incubated at 37° C. for 30 minutes. The plates were then washed $\times$ 3 with PBST, and 0.2 ml amounts of a 1:2000 dilution of goat anti-human (GAH) peroxidase enzyme conjugate (Organon Teknika, Cappel, Melvern, Pa., U.S.A.) that recognized human IgG, IgA, and IgM were added to each well, and the plates were incubated for 30 minutes at 37° C. The plates were then washed×3 with PBST and incubated with 0.2 ml/well substrate consisting of 0.1M citric acid pH 5.2, 0.1 mg/ml o-phenylene diamine, 0.01% $H_2O_2$, at room temperature in the dark for 10 minutes. Reactions were stopped with 50 microliters of 4N $H_2SO_4$, and the color development was quantitated in a Multiscan plate reader at $A_{492}$. In each series of experiments positive and negative controls were included, and all tests were done in duplicate or quadruplicate. Most peptides and peptide conjugates were initially screened against a 1:101 dilution of pools of HIV positive or HIV negative sera, and the same serum pool was used to allow quantitative comparison of immunoreactivity of different free peptides or peptide-protein conjugates. The above conditions were found to provide optimal test performance and were used in the EIA were found to provide optimal test performance and were used in the EIA examples below.

EXAMPLE 4

Comparison of Immunoreactivity of Natural Sequence Peptides of HIV-1 and HIV-2

The peptides in FIGS. 1 and 5 were synthesized as described in Example 1 and conjugated to KLH or BSA as described in Example 2. These peptide-protein conjugates were coated to polystyrene microtiter plates all at a concentration 10 micrograms peptide/ml and evaluated for immunoreactivity as described in Example 3, using a 1:101 dilution of a pool of sera (HIV+/SIV+, respectively) containing antibodies to HIV-1 (FIG. 1) or to HIV-2 (FIG. 5), as well as pooled serum (HIV−-/SIV−, respectively) containing no antibodies to HIV-1 or HIV-2. Significant immunoreactivity was observed with HIV-1 antibodies for BSA-SMCC conjugates of peptides 2S04, 4S25, 3S36, 2S06, 2S07, 2S09, 2S11, 3S51, 2S13, 3S55, and 2S15 (FIG. 1) with slightly superior immunoreactivity for the conjugate of peptide 2S09 with the sequence IWGCSGKLICTTAVPGC. Since sera from patients infected with HIV-2 are relatively unavailable in the United States, the immunoreactivity of HIV-2 synthetic peptides was assessed using serum from macaques infected with SIV, obtained from the University of Washington Primate Center, Seattle, Wash., U.S.A. The AA sequence of SIV is nearly identical to HIV-2 in the region of the peptides synthesized (see Myers et al., *Human Retroviruses and AIDS*, 1988. *A compilation of nucleic acid and amino acid sequences.* Los Alamos National Laboratory, Los Alamos, N. Mex., 87545, USA). Significant immunoreactivity was observed with SIV/HIV-2 antibodies for BSA-SMCC conjugates of peptides 2S23, 2S24, 2S25, 2S27, and 2S28, with best immunoreactivity observed for 2S24 (with the sequence DQARLNSWGCAFRQVC), 2S25 (with the sequence ARLNSWGCAFRQVCHGC), and 2S27 (with the sequence SWGCAFRQVCHTTVPGC) as shown in FIG. 5. In general, better immunoreactivity was observed with BSA than with KLH conjugates.

EXAMPLE 5

A. Evaluation of Immunoreactivity of KLH-MBS Conjugates of Peptides 2S06 and 2S09

FIG. 10A illustrates the immunoreactivity of synthetic natural peptides 2S06 and 2S09 (FIG. 1) when conjugated via their C-terminal GC spacer to KLH using the heterobifunctional linker MBS. Forty-two of the serum specimens contained, and 52 did not contain, antibodies to HIV-1 as determined by the Genetic Systems EIA performed by the Seattle King County Health Department, from whom the serum samples were obtained. All positive samples were discriminated from negatives. However, the immunoreactivity of many of the positives was low ($A_{492}$ less than 1.0), and some of the negative samples had $A_{492}$ values slightly above 0.20, resulting in minimal discrimination between negatives and positives. This poor discrimination led to a search for an improved carrier protein and/or linker.

B. Evaluation of Immunoreactivity of BSA Conjugates of Peptides 2S09 and 5S67

Figure 10B:
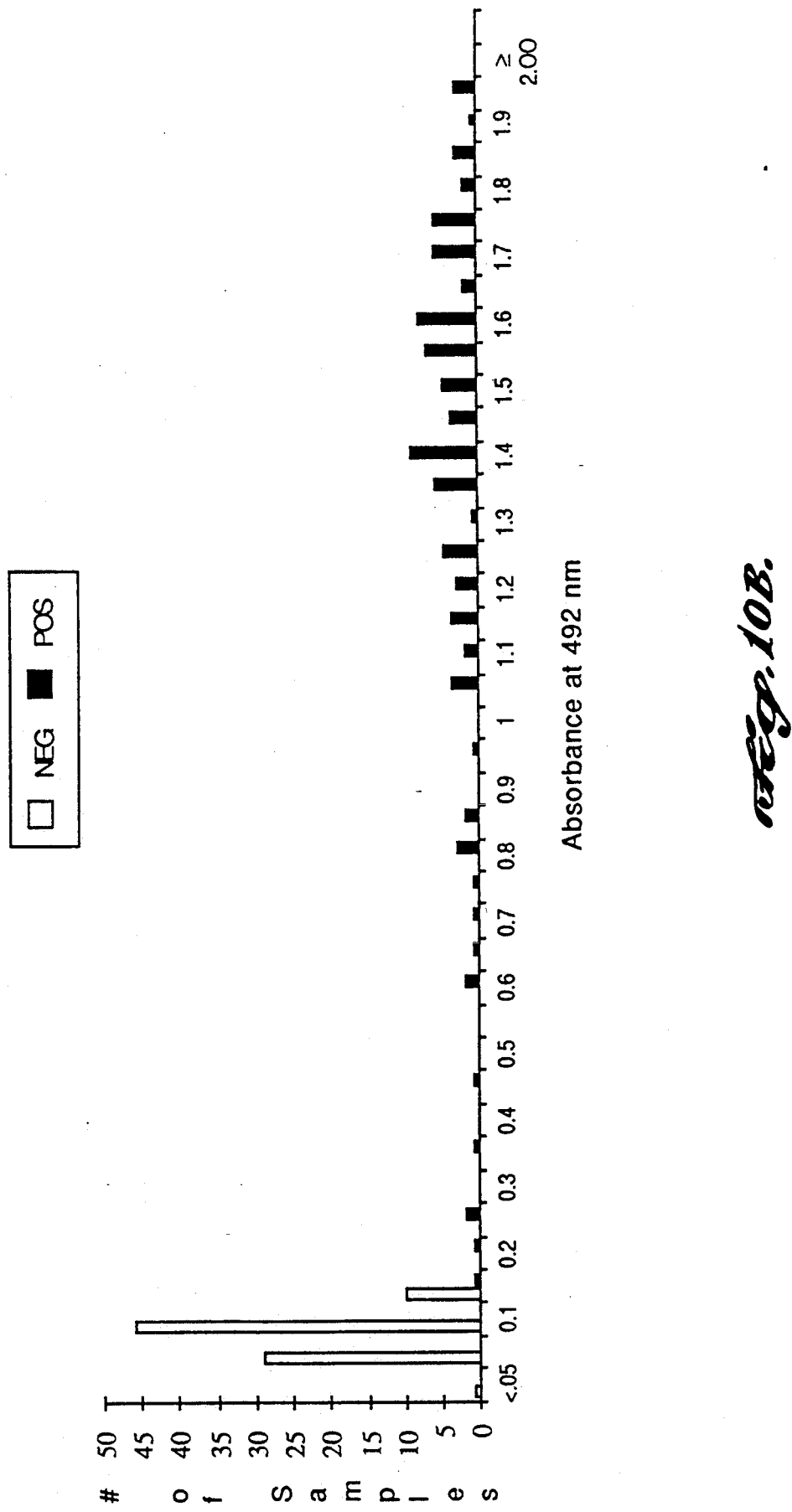
Figure 10C:
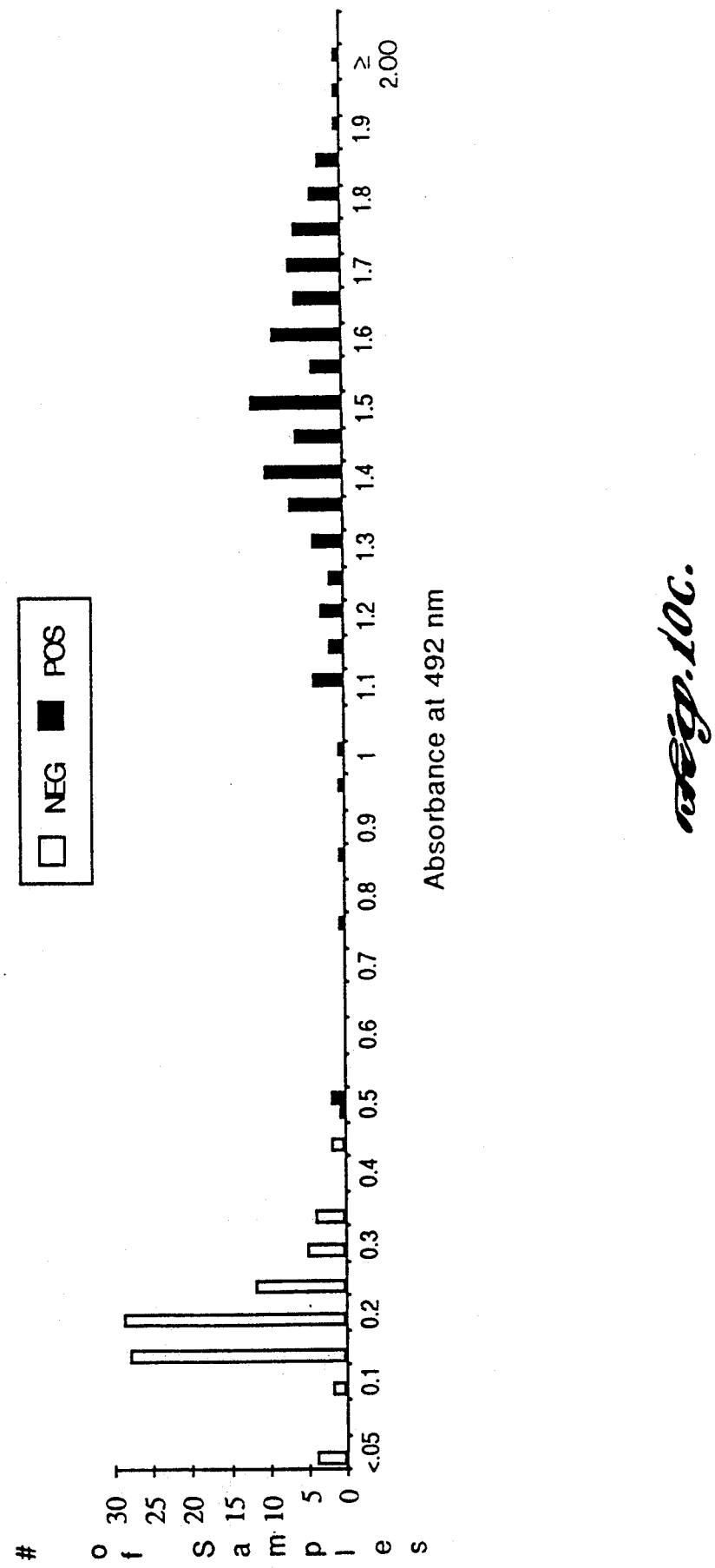

FIG. 10B illustrates the reactivity of synthetic natural peptide IWGCSGKLICTTAVPGC (2S09) when conjugated through its C-terminus to BSA via the heterobifunctional linker SMCC. A total of 184 human sera were tested, 98 of which contained and 86 of which did not contain antibodies to HIV-1, as determined by the Genetic Systems EIA performed by the Seattle King County Health Department, from whom the samples were obtained. Improvement in assay performance as compared with results of Example 5A is noted with respect to negative samples having lower $A_{492}$ values, and most positive samples having higher $A_{492}$ values. This indicated that the peptide-BSA conjugates using SMCC linker gave superior EIA test performance to the peptide-KLH conjugate with MBS as a linker. However, some positive samples had very low immunoreactivity with this conjugate, too low to adequately discriminate them from the negative samples. Because of the possibility that some of the low responsiveness might be due to antigenic differences of genetic variants in the region of this epitope, as reported for HIV isolates from Zaire (Gnann et al., *Science* 237:1346–1349, 1987), the natural sequence variant peptide 5S67 (FIG. 3) was synthesized, chemically linked to BSA with SMCC, and tested against the same sera, plus one additional negative serum sample (FIG. 10C). Many of the patient sera that gave low immunoreactivity with the natural 2S09-BSA conjugate showed higher reactivity with the 5S67-BSA conjugate. However, peptide 5S67 showed unacceptable high reactivity with sera that did not contain antibodies to HIV-1 (FIG. 10C). This instigated a search for unnatural sequence variants of peptide 2S09 that would retain high immunoreactivity with most sera that contained antibodies to HIV-1, and yet retain low reactivity with sera devoid of antibodies to HIV.

EXAMPLE 6

Synthesis and Initial Evaluations of Unnatural Sequence Variants of HIV-1 gp41 Immunoreactive Peptides FIGS. 2 and 3 show 47 sequence variants of peptides 2S09 and 5S67 that were synthesized using the procedure of Example 1. The highlighted amino acids are variants from the natural sequence of these peptides. Those that retained immunoreactivity with human antibodies to HIV-1 were identified by their ability as free peptides to inhibit the binding of these antibodies to the BSA-SMCC conjugates of natural peptides 2S09 and 5S67 bound to polystyrene microtiter plates. FIG. 4 shows the direct antibody binding activity of 7 natural sequence variants and the 21 unnatural sequence variants that showed highest immunoreactivity in FIGS. 2 and 3. Those conjugates with the best ratios of $A_{492}$ immunoreactivity with positive serum pool/$A_{492}$ immunoreactivity with negative serum pool, were further evaluated. Some conjugates of unnatural peptides gave higher immunoreactivity than peptide 2S09 when tested with the least immunoreactive sera from FIG. 10B, but some of these showed increased non-specific reactivity with negative sera, as was seen with peptide 5S67 (FIG. 10C). Other peptides retained immunoreactivity for most positive sera without a change in immunoreactivity for negative sera. Two particularly preferred unnatural sequence peptides, 4S36 and 5S76, were evaluated further.

EXAMPLE 7

Evaluation of Immunoreactivity of BSA Conjugates of Peptides 4S36 and 5S76

Figure 11A:
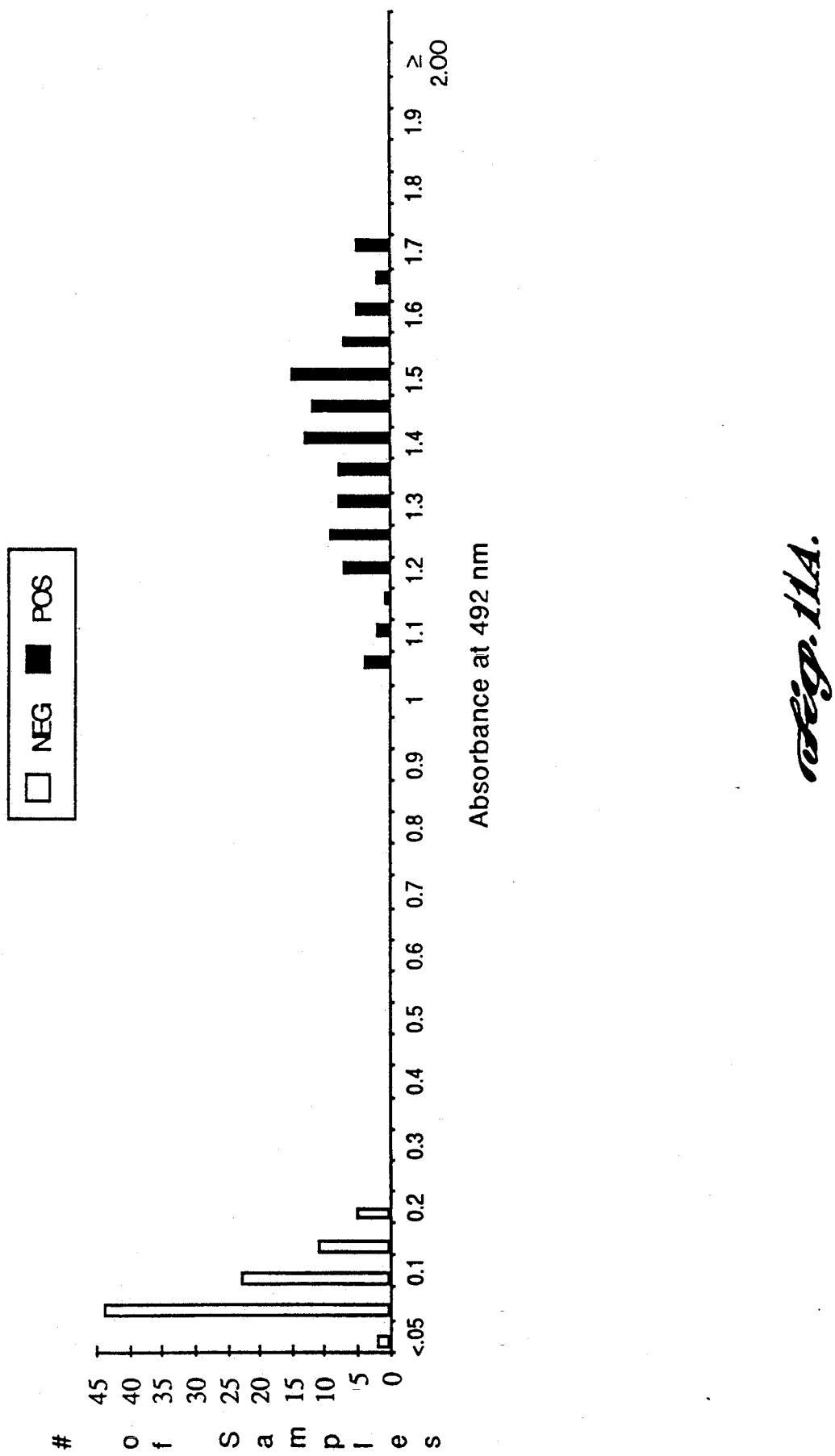
Figure 11B:
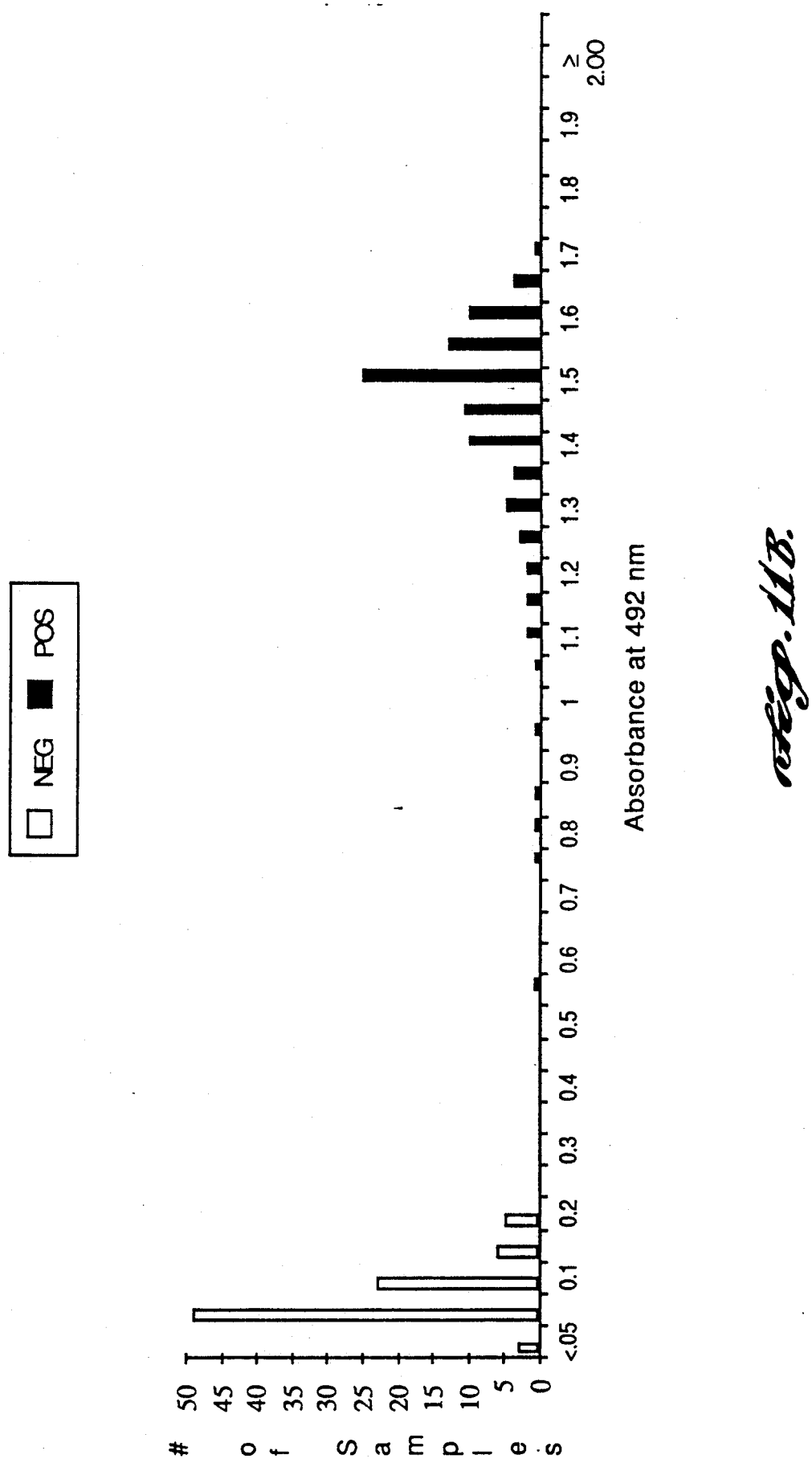
Figure 11C:
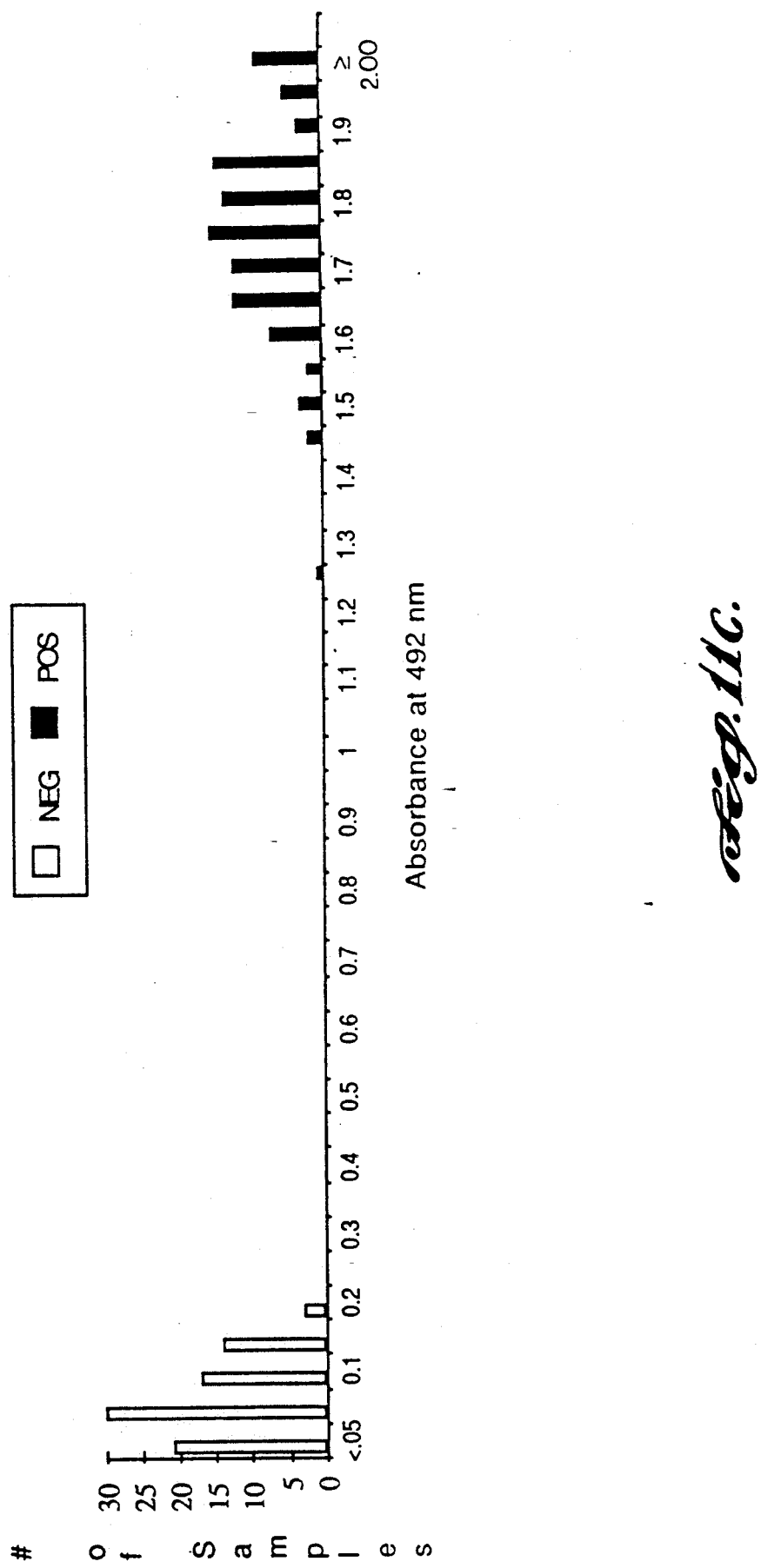

FIG. 11A illustrates the immunoreactivity of unnatural peptide 4S36 (VWGCSGKLICTTAVPGC), when chemically linked via its C-terminus to BSA with the heterobifunctional linker SMCC, coated to polystyrene microtiter plates and tested by EIA with 183 human sera. The same 98 positive sera, and 85 of the 86 negative sera from FIG. 10B were used. A striking increase in immunoreactivity of the low positives was observed as compared to the natural sequence peptide with the same sequence except for the Valine substitution for Isoleucine at the N-terminus of the peptide. Of the 98 positive samples, none gave $A_{492}$ values less than 1.0, whereas the $A_{492}$ values of negative sera remained acceptably low. FIG. 11B illustrates the immunoreactivity of a similar C-terminal BSA-SMCC conjugate of unnatural peptide 5S76 (IWGCSGKMICTTAVPGC), coated to polystyrene microtiter plates and tested by EIA with the same positive and negative sera as FIG. 10B, plus one additional negative serum. Five positive samples gave $A_{492}$ less than 1.0, but the remaining values were high, including strong immunoreactivity with some sera that reacted weakly in FIG. 10B. FIG. 11C illustrates the immunoreactivity with BSA-SMCC conjugates of combined unnatural peptides 4S36 and 5S67, when coated to polystyrene microtiter plates and tested by EIA with the same sera as in FIG. 11A. Reactivity with the negative sera remained low, but immunoreactivity of the positive sera with the combined unnatural peptides was greater than with either peptide alone, resulting in no positive samples with $A_{492}$ values less than 1.25, and a separation in $A_{492}$ values between the lowest positive and the highest negative of more than 1.0 absorbance unit. These EIA test performance results were superior to any other EIA reagent configuration tested on the same test sera and were superior to results previously described in the literature.

EXAMPLE 8

Immunoreactive Specificity of BSA Conjugates of Peptides 4S36 and 5S76

The results in FIG. 11C illustrate superior assay performance and excellent sensitivity by using a combination of two or more synthetic unnatural gp41 peptides conjugated via their C-termini to BSA or other carrier protein. To evaluate how the specificity of such an assay might compare to commercially licensed immunoassays, 12 human sera were obtained from the King County Health Department in Seattle that gave false positive reactions with the commercially available EIA assays for the detection of antibodies to HIV of either or both of Genetic Systems (Seattle, Wash., U.S.A.) or DuPont (Wilmington, Del., U.S.A.) Though positive in these commercial EIA systems, the Western Blot confirmatory test with each of these sera was completely negative.

The 12 human sera panel was assayed using the procedure of Example 3 with a combination of the synthetic peptides 4S36 and 5S76, and compared with results from assaying the same panel with the commercial Genetic Systems and DuPont EIA assays. The results are shown in the following Table 1:

TABLE 1

| | Reactivity with False Positive* Human Sera | | |
|---|---|---|---|
| Serum No. | Reactivity by EIA with Commercially Licensed Genetic Sys | DuPont | Reactivity (A492) with Unnatural Peptides 4S36 & 5S76 |
| 1 | + | + | 0.15 |
| 2 | + | − | 0.20 |
| 3 | − | + | 0.18 |
| 4 | + | − | 0.20 |
| 5 | + | − | 0.14 |
| 6 | + | + | 0.11 |
| 7 | + | + | 0.18 |
| 8 | + | + | 0.06 |
| 9 | + | − | 0.09 |
| 10 | + | + | 0.07 |
| 11 | + | + | 0.70 (positive) |
| 12 | + | − | 0.18 |
| TOTAL FALSE POSITIVE* | 11 | 7 | 1 |
| % FALSE POSITIVE | 92 | 58 | 8 |

*Negative by Western Blot.

Table 1 illustrates the immunoreactivity of an EIA employing BSA conjugates of unnatural synthetic peptides 4S36 and 5S67 to coat the polystyrene plates. Only one of the 12 samples (8%) was positive in the assay employing peptides 4S36 and 5S76, as compared to 7 to 12 (58%) and 11 of 12 (92%) for the DuPont and Genetic Systems commercially licensed assays respectively. These results indicate superior specificity of the EIA test as configured for Example 8 and FIG. 11C as compared to the two commercially available assays.

EXAMPLE 9

Detection of Seroconversion for HIV-1 Antibodies employing BSA Conjugates of 4S36 and 5S76

The immunoreactivity of combined peptide-BSA conjugates of unnatural peptides 4S36 (VWGCSGKLICTTAVPGC) and 5S76 (IWGCSG-KMICTTAVPGC) when linked via their C-termini to BSA employing SMCC according to the procedure of Example 2, and employed in an immunoassay according to the procedure of Example 3 was evaluated on a panel ("Panel A") of nine separate sera collected from a single person who had become infected with HIV-1, purchased from Boston Biomedica, Inc. ("BBI"), Boston, Mass., U.S.A. The BBI seroconversion Panel A was also tested using commercially available EIA assays following the manufacturer's product protocols for EIA assays of the following companies: Abbott Laboratories, Inc. ("Abbott"), Cellular Products Corporation ("Cell Pro"), DuPont Corporation ("DuPont"), Electronucleonics, Inc. ("ENI"), Genetic Systems Corporation ("Gen Sys"), Ortho Diagnostics Corporation ("Ortho") and Organon Teknika, Inc. ("Org Tek"). Panel A allows direct comparison of the immunoreactivity of commercially licensed test for antibody to HIV-1, with the immunoreactivity of two unnatural synthetic peptides of the invention when used as a C-terminal conjugate with BSA. The results are shown in the following Table 2:

TABLE 2

Detection of Development Antibodies to HIV-1 (Seroconversion) in a Plasma Donor

| Sample I.D. PANEL A | Collection Date | anti-HIV | | | | | | | 4S36/ 5S76 | 4S36/ 5S70 Rapid Test |
|---|---|---|---|---|---|---|---|---|---|---|
| | | Abbott | Cell Prod | DuPont | ELISA ENI | Gen Sys | Ortho | Org Tek | | |
| BBI-01 | 05-04-81 | − | − | − | − | − | − | − | − | − |
| BBI-02 | 07-08-81 | − | − | − | − | − | − | − | − | − |
| BBI-03 | 07-29-81 | − | − | − | − | − | − | + | +/− | − |
| BBI-04 | 08-19-81 | + | + | + | + | + | + | + | + | + |
| BBI-05 | 09-02-81 | + | + | + | + | + | + | + | + | + |
| BBI-06 | 09-09-81 | + | + | + | + | + | + | + | + | + |
| BBI-07 | 09-16-81 | + | + | + | + | + | + | + | + | + |
| BBI-08 | 09-02-81 | + | + | + | + | + | + | + | + | + |
| BBI-09 | 10-14-81 | + | + | + | + | + | + | + | + | + |

As shown in Table 2, the combined unnatural peptide conjugate was equally sensitive to 6 commercially licensed tests including Abbott, DuPont, ENI, Gen Sys, and Ortho, using data supplied by BBI for the reactivity in the other tests. Sample number 3 of the nine sera showed a twofold increase in $A_{492}$ as compared to samples 1 and 2, a level insufficient to be definitive, indicating possible lower sensitivity than the Org Tek immunoassay with the seroconversion panel. Also shown in Table 2 are results of testing these sera with BSA conjugates of peptides 4S36 and 5S70 in a rapid test format, as is more fully described in Example 16. These conjugates showed sensitivity equal to 6 commercially available tests even though a rapid test format was employed.

EXAMPLE 10

Synthesis and Evaluations of Sequence Variants of gp32 Peptides of HIV-2

The synthetic peptides shown in FIG. 6 were synthesized according to the procedure of Example 1 and evaluated for immunoreactivity in accordance with the procedure of Example 3.

FIG. 6 illustrates the ability of free peptides of three natural sequence variants and six unnatural sequence variants of peptide 2S27 to inhibit the binding of antibodies to the BSA conjugate of peptide 2S27. Four unnatural sequence variants 5S88, 5S90, 5S91 and 5S92 were found to have significant immunoreactivity.

EXAMPLE 11

Immunoreactivity of Natural and Unnatural Sequence Peptides of HIV-2

The immunoreactivity of the most immunoreactive natural and unnatural sequence variants of HIV-2 from FIGS. 5 and 6 was evaluated with macaque sera containing or not containing antibodies to HIV-2 according to the procedure of Example 3 using peptides conjugated as in Example 2. The results are shown in FIG. 7. Both the natural and unnatural sequence variants in these Figures were able to readily discriminate positive from negative samples with most favorable performances observed with 2S24, 2S25, 2S27, 5S85, 5S86, and 5S92. Further evaluation of the best of these natural and unnatural peptides may be conducted by testing larger numbers of sera, including serum samples from West African patients infected with HIV-2.

EXAMPLE 12

Sensitivity of Detection of Seroconversion for HIV-2 Antibodies

The immunoreactivity of the HIV-2 peptide BSA conjugates 2S24, (2S24 plus 5S86), and 5S92 was evaluated for detection of seroconversion in macaques using serial sera collected over a 16 week period from 7 macaques experimentally infected with SIV at week 0. The results are shown in the following Table 3:

TABLE 3

Detection of Development of Antibodies to HIV-2 (Seroconversion) in 7 Macaques experimentally infected with SIV.*

| | Reactivity by Peptide-BSA Conjugate | | |
|---|---|---|---|
| Sample | 2S24 | 2S24 + 5S86 | 5S92 |
| Week 0* | 0/7 | 0/7 | 0/7 |
| Week 1 | 0/7 | 0/7 | 0/7 |
| Week 2 | 1/7 | 1/7 | 1/7 |
| Week 3 | 2/7 | 3/7 | 3/7 |
| Week 4 | 4/7 | 4/7 | 3/7 |
| Week 6 | 6/7 | 6/7 | 6/7 |
| Week 8 | 7/7 | 7/7 | 6/7 |
| Week 12 | 7/7 | 7/7 | 7/7 |
| Week 16 | 7/7 | 7/7 | 7/7 |

*Six Animals Infected by HIV injection of SIV at Week 0. One Animal that did not seroconvert until week 8–12 received intrarectal inoculation of SIV at week 0.

As shown in Table 3, each conjugate detected seroconversion. The most sensitive EIA used a combination of peptides 2S24 and 5S86 conjugated via their C-termini to BSA.

EXAMPLE 13

Immunoreactivities of HIV-1 peptide conjugates with HIV-2 serum and Vice Versa The peptides 4S36 (VWGCSGKLICTTAVPGC) and 5S76 (IWGSGKMICTTAVPGC), which correspond to HIV-1 gp41 peptides, were linked via their C-termini to BSA according to the procedure of Example 2, and then employed in an EIA as in Example 3, to test 30 HIV-1 antibody positive, 23 HIV-2/SIV antibody positive, 15 HIV-1 antibody negative, and 15 HIV-2/SIV antibody negative sera. As shown in FIG. 13A, the conjugated peptides 4S36 and 5S76 detected only the HIV-1 antibody positive samples, and missed all 23 HIV-2 antibody positive samples. The peptides 2S24 (DQARLNSWGCAFRQVC) and 5S86 (SWGCAFRQVCHTSVPGC), which correspond to HIV-2/SIV natural peptides, were linked via their C-termini to BSA, according to the procedure of Example 2, and then employed in an EIA according to the procedure of Example 3 to test the sera panel described above. As shown in FIG. 13B, the conjugated peptides 2S24 and 5S86 detected all 23 HIV-2 antibody positive samples, and 4 of the 30 HIV-1 antibody positive samples gave A492 values of 0.4 or above. The conjugated peptides 4S36 and 5S76 were then combined with the conjugated peptides 2S24 and 5S86 and employed by an EIA to test the same sera panel. As shown in FIG. 13C, the HIV-1 plus HIV-2 combined antigen plate detected all HIV-1 and HIV-2 antibody positives. All HIV-1 or HIV-2 antibody negative sera were negative with all three antigen test combinations.

EXAMPLE 14

Immunoreactivity of p24 synthetic peptides with serum pools and individual sera FIG. 8 illustrates the immunoreactivity and AA sequences of synthetic peptides of the p24 protein of HIV-1, when conjugated to BSA via their C-termini using SMCC, and reacted with a pool of approximately 50 sera from persons containing antibody to HIV-1, or with a pool of approximately 30 sera from individuals devoid of antibody to HIV-1. As illustrated in the Figure, only the pool comprised of peptides 5S93–5S96 showed significant immunoreactivity, and specifically only peptide 5S94 within that pool, with the sequence ALGPAATLEEMMTACGC proved to be the immunoreactive peptide. This peptide linked via its C-terminus to BSA using SMCC as the linker was tested against 98 individual sera that contained, and 85 individual sera that did not contain antibodies to HIV-1. No negative sera (0/85, 0%) reacted, and 17 positive sera (17/98, 17%) were immunoreactive. It has been reported that individuals lose antibodies to p24 during the course of progression from asymptomatic infection to clinical disease and AIDS (Franchini et al., Blood 69:(2):437–441, 1987, and Weber et al., Lancet i:119–122, 1987), which may explain the lower frequency of antibodies to this peptide in the sera tested.

EXAMPLE 15

Rapid Tests For Detection of Antibodies to HIV

Figure 15:
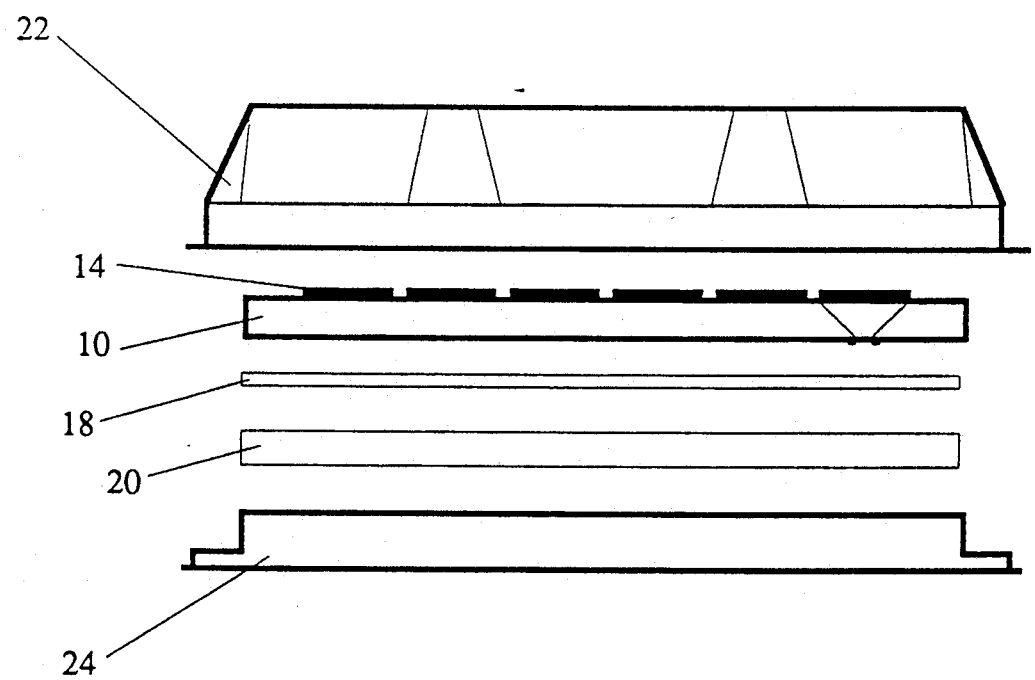

A test device for performing rapid tests in less than 15 minutes was prepared as illustrated in FIGS. 14 and 15. Referring to FIGS. 14 and 15, the device comprises a plastic slide 10 (approximately 1 inch wide by 3/16 inch thick by 3¼ inches long) having a plurality of funnel-like wells 12, each having a capacity of approximately 200 microliters, an upper inflow tract rim 14 diameter of approximately 9 mm and a lower outflow tract 16 diameter of approximately 2 mm. The undersurface of the outflow tract 16 is designed so as to provide a smooth even contact with a membrane filter 18 placed next to it in the apparatus. The membrane filter separates reactants passing through it by size, retaining those particles above a predetermined size, such as above 0.22 microns, or above 0.45 microns in size (depending upon the specific filter chosen), through other filters placed into the apparatus might separate by binding or affinity (i.e. nitrocellulose, glass). Beneath the filter membrane is an absorbent pad 20 of sufficient thickness and absorbent capacity to absorb all of the liquid placed into the well. These three components are encased within a plastic holder 21 comprising a top piece 22 and bottom support 24. The two parts of the case fit together by friction, and serve to hold the slide, filter membrane and absorbent pad closely approximated to each other for performance of the test.

Free peptide 2S09 (IWGCSGKLICTTAVPGC) and peptide 2S09 conjugated via its C-terminus to BSA using SMCC as the linker (in accordance with the procedure of Example 2), were reacted with colloidal gold (20 nanometer size particles, Janssen Life Sciences, Piscataway, N.J., U.S.A.). Despite numerous efforts, free peptide could not be used alone with the colloidal gold. It behaved like an electrolyte, causing the colloidal gold to immediately fall out of solution. Several different free peptides were added to colloidal gold size 20 nm and the results were the same. The 20 nm gold particles immediately fell out of solution indicating that this effect was not peptide specific. The 2S09 peptide-BSA conjugate behaved much more like BSA alone, and it was possible to prepare peptide-BSA-Au conjugates as follows:

An 8 ml quantity of peptide IWGCSGKLICTTAVPGC ($A_{280\ nm} \sim = 0.50$) conjugated via its C-terminus and SMCC to BSA was dialyzed overnight against 2L of DI water at 4° C. Two ml amounts of colloidal gold sol of 20 nm (G20, Janssen Life Sciences) diameter were adjusted to pH 5.0, 5.2, 5.5, 5.8, 6.0, 6.1, and 6.4 using 0.2N $K_2CO_3$ and 0.2N $H_3PO_4$. A preliminary check for protection against flocculation was made with 200 microliter amounts of each pH adjusted gold sol solution in a microtiter plate. Twenty microliters of the dialyzed peptide conjugate were added with mixing to each pH adjusted gold sol solution without resultant color change, and allowed to stand for 2 minutes. The same gold sol solutions in a duplicate set of microtiter wells were prepared as controls and received buffer in place of the peptide-protein conjugate. Fifty microliters of 10% NaCl were added to each well. Those without peptide-BSA turned grey as evidence of flocculation of the gold sol, and the others stayed their original color. The $A_{580}$ of each well was determined and the lowest values, indicating best protection, were at pH6.1 > pH6.0 >> other pH's. Using larger amounts of gold sol at pH6.1 the minimal amount of protective protein was determined to be 70 microliters of the dialyzed peptide-BSA ($A_{280} = 0.45$). The dialyzed peptide-BSA at pH6.1 was ultracentrifuged at 150,000×g for 70 min to remove aggregates and the minimal protective protein study was repeated with the supernate of the ultracentrifugation with the same results. An 85 microliter amount of peptide-BSA per ml of G20 gold sol was chosen for protection, and 15 ml of ultracentrifuge supernate were added to 176 ml of gold sol with vigorous stirring for 2.5 minutes, followed by adjustment of the pH to 9.0 with 0.2N $K_2CO_3$, and addition of pH 9 10% BSA to a final concentration of 1% BSA. The solutions were then centrifuged at 4° C. for 30 minutes at 12,000×g (avg.). The supernate was aspirated and discarded except for 10% that was retained and used to suspend the pellet. A wash buffer of Tris 20 mM, 150 mM NaCl, 1% BSA, 0.05% $NaN_3$, pH 8.2 was added up to the original volume, and the centrifugation was repeated. The supernate removal, resuspension, repeat washes and centrifugation were repeated twice, with the same wash buffer adjusted to pH 9.0. The $A_{520}$ of the final resuspended solution was 6.68, and the color was a deep red. A control peptide-BSA conjugate was prepared using exactly the same protocol as above, but using as the peptide and mycobacterial protein sequence unrelated to HIV.

To test the immunoreactivity of the peptide-BSA-gold conjugates, 10 microliters of undiluted conjugate were mixed with 20 microliters of human serum diluted 1:100 in 1% NRS, 1% BSA, 50 mM phosphate, 100 mM NaCl, pH 7.4, 0.05% $NaN_3$, and incubated at room temperature for 5 minutes. Twenty microliters of 1% heat-killed *Staphlococcus aureus* Cowan strain I were added to each serum, and incubated an additional 5 minutes at room temperature. 45 microliters of each sample were then placed into a well 12 on the device described above containing a 0.22 micron sizing membrane filter. A total of 40 serum samples were tested, 20 of which contained, and 20 of which did not contain, antibodies to HIV-1. After the fluid of each sample ran through the membrane and into the absorbent pad, red-purple dots were left for 19 of the 20 positive serum samples, and only the white color of the underlying membrane remained for the 20 negative sera and for the mycobacterial peptide-BSA-gold conjugate when used with the positive sera. This test demonstrated the feasibility of a rapid test to detect antibodies to HIV using the device and a peptide-BSA-colloidal-gold conjugate. Furthermore, it demonstrated that free peptides were unacceptable for preparing such conjugates.

EXAMPLE 16

Rapid HIV-1 EIA Test Employing Peptide-BSA Conjugates Immobilized Onto Latex Particles The usefulness of the rapid test device described in Example 15 for performing a rapid EIA test was demonstrated as follows: Unnatural peptides 4S36 (VWGCSGKLICTTAVPGC) and 5S70 (IWGCSGKQICTTAVPGC), as free peptides and as cysteine-linked conjugates to BSA prepared as in example 2, were chemically coupled to carboxylate latex (0.832 micron average diameter, Seragen, Indianapolis, Ind., U.S.A.) according to the following protocol. A 125 microliter volume of 10% latex was added to a 375 microliter volume of deionized water, and mixed with an equal volume (0.5 ml) of 1M carbodiimide, pH 4.5. The mixture was shaken gently a room temperature for 1 hour, and then washed 3 times by centrifugation at 9,000×g for 10 minutes, removal of supernate, and resuspension of the pellet in a 12-14 ml volume of deionized water, pH 4.5. The free peptides at 1 mg/ml concentration (500 micrograms/ml of each peptide 4S36 and 5S70), or the peptide-BSA conjugate of peptides 4S36 and 5S70 at 500 micrograms/ml were added to the final washed activated latex pellet (1 ml volume of peptide containing solution per 125 microliters original volume of latex). The latex peptide mixture was shaken gently overnight at 4° C., and then centrifuged at 9,000×g for 10 minutes, and the supernate removed. Measurement of the $A_{280}$ of the free peptide solution, or of the peptide-BSA conjugate, before and after combination with the activated latex, indicated that 60% of the conjugate, and 45% of the free peptides bound to the latex. The pellets of latex plus attached free peptide or conjugate were washed three times each by centrifugation with a wash buffer consisting of 0.03M Tris, pH 8.0 with 0.8% NaCl, 1% BSA, and 0.05% $NaN_3$. The final washed pellet was resuspended to a latex concentration of 0.625%, using the same wash buffer with the $NaN_3$ concentration adjusted to 0.1% (latex diluent buffer). It was determined that this stock solution of latex coated with peptide-BSA conjugate could be diluted 1:10–1:30 with latex diluent buffer for use in the rapid EIA described below. In contrast, even undiluted the stock of latex coated with free peptides was unable to discriminate between samples containing and not containing antibody to HIV in a rapid EIA format.

Serum specimens were diluted 1:8 for the rapid EIA in a serum diluent buffer consisting of 0.03M Tris, pH 8 containing 0.8% NaCl, 0.05% $NaN_3$, 0.05% Triton x-100. For the assay, one drop of diluted serum (20 microliters) was added to one drop (20 microliters) of 1:10 diluted stock latex, mixed, and allowed to incubate at room temperature in a test tube for 1–2 minutes. One drop (20 microliters) of this mixture was added to the rapid test device of Example 15 that contained a 0.45 micron sizing membrane filter. The mixture flowed almost immediately into the device, and was followed in succession with 1 drop (20 microliters) each of wash (serum diluent buffer). 1 drop alkaline phosphatase conjugate consisting of alkaline phosphatase linked to goat anti human immunoglobulin (gamma chain specific, Cappel-Organon Teknika, Pa. ) diluted 1:20 in latex diluent buffer with added 4 mM $MgCl_2$, 1 drop wash, and 1 drop substrate. The substrate consisted of 100 mM Tris buffer pH 9.6 containing 100 micrograms/ml each of NBT (Nitroblue tetrazolium, Sigma Chem Co., St. Louis, Mo. U.S.A.) and BCIP (5-bromo-4-chloro-3-indoxylphosphate, Sigma). Positives developed a blue-purple precipitate on the membrane, generally within 2 minutes, as shown at 26 in FIG. 14, and negatives remained without a blue color, as shown at 28 in FIG. 14 for at least 5 minutes. The reaction was stopped after 3–4 minutes by adding a drop of 4N $H_2SO_4$, and the test device could be retained as a permanent record of positive (blue-purple color) or negative (white membrane) until the results were recorded. A total of 200 human sera were tested with the rapid EIA, 98 of which contained and 102 of which did not contain antibodies to HIV-1. Ninety-seven of those containing, and none of those not containing antibodies to HIV gave a purple color in the rapid EIA format. This demonstrated that the rapid EIA using the above protocol and the test device could be used to detect antibodies to HIV within 15 minutes. It further indicated that the peptide-BSA conjugates of unnatural peptides 4S36 and 5S70 were suitable for the rapid EIA, but these same peptides were unacceptable when used as free peptides covalently bound to latex via their amino groups for use in the test. Free peptide 4S36 passively adsorbed to latex produced an immunoreactive reagent, though the kinetics of the reaction, and the discrimination between positive and negative samples was less with this reagent than with the latex reagent prepared with peptide-BSA conjugate.

EXAMPLE 17

Rapid EIA Test to Detect Antibodies to HIV-2

The carbodiimide coupling procedures of Example 16 were used to prepare a latex containing covalently bound peptide-BSA conjugate of peptides 2S24, 5S86 and 5S92. In addition free peptide 2S25 was passively adsorbed onto carboxylate latex. $A_{280}$ determinations before and after covalent coupling or passive adsorption indicated that 300 micrograms of the peptide-BSA conjugates, and 230 micrograms of the passively adsorbed peptide 2S25 bound to the 125 microliters of 10% latex. After processing and use as indicated in Example 16, both preparations were found capable of discriminating serum samples containing (HIV-2+) those not containing (HIV-2−) antibodies to HIV-2. However, the reaction kinetics were faster, and better discrimination was observed between serum samples containing and not containing antibodies to HIV-2 with latex prepared from cysteine-linked peptide-BSA conjugates.

EXAMPLE 18

Rapid EIA For Simultaneous Detection of Antibodies to HIV-1 and/or HIV-2

The reagents and test device reaction conditions of Examples 16 and 17 were used. By including a combination of peptide-BSA latex reagents representing both HIV-1 (4S36 and 5S70, FIG. 4) and HIV-2 (2S24, 5S86, and 5S92, FIG. 7) it was possible to detect antibodies to either HIV-1 or HIV-2 with the same reagent. Latex reagents representing only HIV-1 were unable to recognize HIV-2 antibodies in the rapid test and vice versa.

EXAMPLE 19

Confirmation of the Specificity of an Observed Positive Result in the Rapid EIA Test by Inhibition of the Reaction with Non-conjugated Peptide(s).

Table 4 illustrates the results obtained with 10 HIV-1 Antibody Positive and 4 HIV-2 Antibody Positive sera when tested with HIV-1 latex reagent alone, HIV-2 latex reagent alone, and HIV-1 plus HIV-2 latex reagents, either in the presence of or without competing or inhibiting non-conjugated peptides. As expected the latex reagent containing peptide-BSAd conjugate of HIV-1 peptide detected HIV-1 antibodies and not HIV-2 antibodies, and the latex reagent containing peptide-BSA conjugate of HIV-2 peptides detected HIV-2 antibodies but not HIV-1 antibodies. In contrast a combination of both latex reagents detected both antibodies. Free peptides of HIV-1 gp41 identical to those used in the peptide-BSA conjugate inhibited antibody binding to the HIV-1 but not the HIV-2 latex reagent and vice versa. This confirmed that the antibody detected was directed against HIV transmembrane glycoprotein, and further identified whether the antibodies were directed at HIV-1 or alternatively at HIV-2, or both.

TABLE 4

Immunoreactive Specificity of Rapid EIA Test. Confirmation by Inhibition of Immunoreactivity with non-conjugated peptides

| # | Serum Type | Reactivity of Peptide-BSA Latex | | |
|---|---|---|---|---|
| | | HIV-1* | HIV-2** | HIV-1 & HIV-2 |
| 10 | HIV-1 + Alone | 10/10 | 0/10 | 10/10 |

TABLE 4-continued

Immunoreactive Specificity of Rapid EIA Test. Confirmation by Inhibition of Immunoreactivity with non-conjugated peptides

| # | Serum Type | Reactivity of Peptide-BSA Latex | | |
|---|---|---|---|---|
| | | HIV-1* | HIV-2** | HIV-1 & HIV-2 |
| 10 | HIV-1 + plus 100 µg/ml 4S36 & 5S76 | 0/10 | 0/10 | 0/10 |
| 10 | HIV-1 + plus 100 µg/ml 2S25 & 5S86 | 10/10 | 0/10 | 10/10 |
| 4 | HIV-2 + Alone | 0/4 | 4/4 | 4/4 |
| 4 | HIV-2 plus 100 µg/ml 2S25 & 5S86 | 0/4 | 0/4 | 0/4 |
| 4 | HIV-2 plus 100 µg/ml 4S36 & 4S76 | 0/4 | 4/4 | 4/4 |

*Coated with a peptide-BSA conjugate of peptides 4S36 and 5S70 covalently linked via cysteine to bSA
**Coated with a peptide-BSA conjugate of peptides 2S24 and 5S86 covalently linked via cysteine to BSA.

EXAMPLE 20

Use of Peptide-Protein Conjugate of HIV proteins for Immunization of Animals to produce Anti-peptide Polyclonal or Monoclonal Antibodies Peptides are conjugated to KLH as in Example 2 and used to prepare an emulsion in incomplete Freunds adjuvant at a final peptide concentration of 500 µg/ml. This emulsion is administered in 50 µg amounts IP to mice or in 100 µg amounts IM and subscapularly to rabbits. After 1 month booster immunizations at the same dosage level are again administered and the serum of each animal is tested for antibody response to the peptide by EIA employing either free peptide, of peptide linked to BSA with a different heterobifunctional linker (SMCC) than that used to prepare the KLH conjugate (MBS). The polyvalent serum is used either directly or after further booster immunizations, or if monoclonal antibodies were desired standard hybridoma methodologies are subsequently performed (Gillis & Buchanan, Infect Immun 49:371–377, 1982).

What is claimed is:

1. A method of determining the presence or amount of antibodies to HIV-1 in a fluid sample, comprising:
   contacting the fluid sample with at least one synthetic peptide selected from the group consisting of:

| | |
|---|---|
| I W G C S G K L I C T T A V P G C, | (2S09); |
| L W G C S G K L I C T T A V P G C, | (4S35); |
| V W G C S G K L I C T T A V P G C, | (4S36); |
| I Y G C S G K L I C T T A V P G C, | (4S37); |
| I F G C S G K L I C T T A V P G C, | (4S38); |
| I W G C T G K L I C T T A V P G C, | (4S43); |
| I W G C S G R L I C T T A V P G C, | (4S45); |
| I W G C S G K I I C T T A V P G C, | (4S46); |
| I W G C S G K L L C T T A V P G C, | (4S48); |
| I W G C S G K L V C T T A V P G C, | (4S49); |
| I W G C S G K L I C S T A V P G C, | (4S52); |
| I W G C S G K L I C T S A V P G C, | (4S53); |
| I W G C S G K L I C T T G V P G C, | (4S43); |
| I W G C S G K L I C T T A L P G C, | (4S55); |
| I W G C S G K L I C T T A I P G C, | (4S56); |
| F W G C S G K L I C T T T V P G C, | (5S51); |
| I W G C S G K L I C T T T V P G C, | (5S52); |
| F W G C S G K L I C T T A V P G C, | (5S53); |
| I W G C S G H L I C T T N V P G C, | (5S55); |
| I W G C S G K F I C T T T V P G C, | (5S56); |
| M W G C S G K H I C T T F V P G C, | (5S60); |
| I W G C S G K V I C T T A V P G C, | (5S61); |
| I W G C S G K I I C P T N V P G C, | (5S64); |
| I W G C S G K I I C T T A V P G C, | (5S65); |
| I W G C S G K H I C T T T V P G C, | (5S67); |

-continued

| | |
|---|---|
| I W G C S G K Q I C T T A V P G C, | (5S70); |
| I W G C S G K T I C T T A V P G C, | (5S75); |
| I W G C S G K M I C T T A V P G C, | (5S76); |
| I W G C S H K L I C T T A V P G C, | (5S81); |
| V W G C S G K M I C T T A V P G C, | (AB15); |
| G C S G K L I C T T A V P W N G C, | (2S11); |
| C S G K L I C T T A V P W N A G C, | (3S51); |
| S G K L I C T T A V P W N A S G C, | (2S13); |
| G K L I C T T A V P W N A S W G C, | (3S55); |
| K L I C T T A V P W N A S W S G C, | (2S15); | and mixtures thereof; the synthetic peptide being conjugated through its C-terminus to a carrier protein, allowing the at least one synthetic peptide to react with the fluid sample to form a complex if antibodies to HIV-1 are present in the sample, and determining the presence or amount of complex formed as an indication of the presence or amount of antibodies to HIV-1 in the fluid sample.

2. The method of claim 1, wherein the immunospecific reagent comprises at least two synthetic peptides conjugated through their C-termini to a carrier protein.

3. The method of claim 2, wherein the immunospecific reagent comprises at least two synthetic peptides having immunoreactive specificities characteristic of antigenic domains of the gp41 protein of HIV-1.

4. The method of claim 3, wherein the immunospecific reagent comprises at least two peptides selected from the group consisting of 4S36, 5S76, AB14, 2S04, and 2S09.

5. The method of claim 1, wherein the immunospecific reagent is bound to a solid phase.

6. An immunospecific reagent comprising at least one synthetic peptide, conjugated through its C-terminus to a carrier protein, the synthetic peptide being selected from the group consisting of:

| | |
|---|---|
| I W G C S G K L I C T T A V P G C, | (2S09); |
| L W G C S G K L I C T T A V P G C, | (4S35); |
| V W G C S G K L I C T T A V P G C, | (4S36); |

-continued

| | |
|---|---|
| I Y G C S G K L I C T T A V P G C, | (4S37); |
| I F G C S G K L I C T T A V P G C, | (4S38); |
| I W G C T G K L I C T T A V P G C, | (4S43); |
| I W G C S G R L I C T T A V P G C, | (4S45); |
| I W G C S G K I I C T T A V P G C, | (4S46); |
| I W G C S G K L L C T T A V P G C, | (4S48); |
| I W G C S G K L V C T T A V P G C, | (4S49); |
| I W G C S G K L I C S T A V P G C, | (4S52); |
| I W G C S G K L I C T S A V P G C, | (4S53); |
| I W G C S G K L I C T T G V P G C, | (4S54); |
| I W G C S G K L I C T T A L P G C, | (4S55); |
| I W G C S G K L I C T T A I P G C, | (4S56); |
| F W G C S G K L I C T T T V P G C, | (5S51); |
| I W G C S G K L I C T T T V P G C, | (5S52); |
| F W G C S G K L I C T T A V P G C, | (5S53); |
| I W G C S G H L I C T T N V P G C, | (5S55); |
| I W G C S G K F I C T T T V P G C, | (5S56); |
| M W G C S G K H I C T T F V P G C, | (5S60); |
| I W G C S G K V I C T T A V P G C, | (5S61); |
| I W G C S G K I I C P T N V P G C, | (5S64); |
| I W G C S G K I I C T T A V P G C, | (5S65); |
| I W G C S G K H I C T T T V P G C, | (5S67); |
| I W G C S G K Q I C T T A V P G C, | (5S70); |
| I W G C S G K T I C T T A V P G C, | (5S75); |
| I W G C S G K M I C T T A V P G C, | (5S76); |
| I W G C S H K L I C T T A V P G C, | (5S81); |
| V W G C S G K M I C T T A V P G C, | (AB15); |
| G C S G K L I C T T A V P W N G C, | (2S11); |
| C S G K L I C T T A V P W N A G C, | (3S51); |
| S G K L I C T T A V P W N A S G C, | (2S13); |
| G K L I C T T A V P W N A S W G C, | (3S55); and |
| K L I C T T A V P W N A S W S G C, | (2S15); | and mixtures thereof.

7. An immunospecific reagent of claim 6, comprising at least two synthetic peptide having an immunoreactive specificity characteristic of gp41 of HIV-1.

8. The immunospecific reagent of claim 7, comprising at least two peptides selected from the group consisting of 4S36, 5S76, AB14, and 2S09.

9. A diagnostic kit comprising at least one immunospecific reagent of claim 6, together with a label for assisting in the detection of the formation of reagent/antibody complexes when the reagent is contacted with a fluid sample containing antibodies having binding specificity to HIV-1.

* * * * *

UNITED STATES PATENT AND TRADEMARK OFFICE
CERTIFICATE OF CORRECTION

PATENT NO. : 5,260,189
DATED : November 9, 1993
INVENTOR(S) : C. Formoso et al.

It is certified that error appears in the above-indentified patent and that said Letters Patent is hereby corrected as shown below:

| COLUMN | LINE | |
|---|---|---|
| 7 | 49 | after "may" insert --not bind well to solid surfaces, or the epitopes of the small peptides may-- |
| 9 | 2 & 3 | "IWGCSGKLICT-TAVPGC" should read --IWGCSGKLICTTAVPGC-- |
| 9 | 9 & 10 | "ARLNSW-GCAFRQVCHGC" should read --ARLNSWGCAFRQVCHGC-- |
| 9 | 15 | "ALGPAATLEEMMTACGC" should read --ALGPAATLEEMMTACGC-- |
| 10 | 11 | "(Examples 15-19Table 4)" should read --(Examples 15-19, Table 4)-- |
| 10 | 47 | "FIGS. 2-4, 6 7" should read --FIGURES 2-4, 6, 7-- |
| 14 | 10 | "N-alphaamino" should read --N-alpha-amino-- |
| 17 | 18 | after "EIA" delete "were found to provide optimal test performance and were used in the EIA" |
| 18 | 21 | after "County" continue the sentence within the same paragraph |

UNITED STATES PATENT AND TRADEMARK OFFICE
CERTIFICATE OF CORRECTION

PATENT NO. : 5,260,189
DATED : November 9, 1993
INVENTOR(S) : C. Formoso et al.

It is certified that error appears in the above-indentified patent and that said Letters Patent is hereby corrected as shown below:

| COLUMN | LINE | |
|---|---|---|
| 20 | 54 | after "7" delete "to" and insert --of-- |
| 21 | 17 | "test" should read --tests-- |
| 27 | 48 | "peptide-BSAd" should read --peptide-BSA-- |
| 28 | 58 | "IWGCSGKLICTTGVPGC, (4S43)" should read --IWGCSGKLICTTGVPGC, (4S54)-- |

Signed and Sealed this

Nineteenth Day of April, 1994

BRUCE LEHMAN

Attesting Officer     Commissioner of Patents and Trademarks